US009202605B2

(12) United States Patent
Kobayashi et al.

(10) Patent No.: US 9,202,605 B2
(45) Date of Patent: Dec. 1, 2015

(54) ORGANIC TRANSPARENT ELECTRODE, METHOD FOR PRODUCING ORGANIC TRANSPARENT ELECTRODE, TOUCH PANEL, DISPLAY, ORGANIC METAL, METHOD FOR PRODUCING ORGANIC METAL, COMPOUND OR SALT THEREOF, ELECTRIC WIRE AND ELECTRONIC DEVICE

(71) Applicant: National Institute for Materials Science, Ibaraki (JP)

(72) Inventors: Yuka Kobayashi, Ibaraki (JP); Takeshi Terauchi, Ibaraki (JP); Satoshi Sumi, Ibaraki (JP)

(73) Assignee: National Institute for Materials Science, Ibaraki (JP)

( * ) Notice: Subject to any disclaimer, the term of this patent is extended or adjusted under 35 U.S.C. 154(b) by 0 days.

(21) Appl. No.: 14/373,256

(22) PCT Filed: Jul. 17, 2013

(86) PCT No.: PCT/JP2013/069451
§ 371 (c)(1),
(2) Date: Jul. 18, 2014

(87) PCT Pub. No.: WO2014/057721
PCT Pub. Date: Apr. 17, 2014

(65) Prior Publication Data
US 2015/0005511 A1    Jan. 1, 2015

(30) Foreign Application Priority Data

Oct. 13, 2012    (JP) .................................. 2012-227532
Oct. 21, 2012    (JP) .................................. 2012-232451

(51) Int. Cl.
*H01B 1/12*    (2006.01)
*C07D 495/04*    (2006.01)
*G06F 3/00*    (2006.01)
*H01L 51/00*    (2006.01)
*H01L 51/44*    (2006.01)

(52) U.S. Cl.
CPC ................ *H01B 1/12* (2013.01); *C07D 495/04* (2013.01); *G06F 3/00* (2013.01); *H01B 1/127* (2013.01); *H01L 51/0051* (2013.01); *H01L 51/441* (2013.01)

(58) Field of Classification Search
CPC ........................................................ H01B 1/12
USPC ........................................................ 549/7, 32
See application file for complete search history.

(56) References Cited

U.S. PATENT DOCUMENTS 4,900,842 A    2/1990    Robin et al.

FOREIGN PATENT DOCUMENTS

JP    2010-027600 A    2/2010

OTHER PUBLICATIONS

King, Med. Chem., Principle and Practice (1994), pp. 206-208.*
Akamatu et al., "Electrical Conductivity of the Perylene-Bromine Complex," Nature, 173: 168-169 (1954).
Furukawa et al., "Novel Type of Career Generated System: Magnetic Investigations of TTF-Based Self-Doped Hydrogen-Bonding Conductor," Journal of the Physical Society of Japan, 79: 053701-1-053701-4 (2010).
Kirtley et al., "Organic Electronics: When TTF met TCNQ," Nature Materials, 7: 520-521 (2008).
Kobayashi et al., "Synthesis, characterization, and dc conductivity of hydrogen-bonding dibenzotetrathiafulvalene (DBTTF) based salts," Synthetic Metals, 160: 575-583 (2010).
Kobayashi et al., "Hydrogen-Bonding-Assisted Self-Doping in Tetrathiafulvalene (TTF) Conductor," Journal of the American Chemical Society, 131: 9995-10002 (2009).
Kobayashi et al., "Hydrogen-bonding tetrathiafulvalene (TTF) conductors: Carrier generation by self-doping," Physica B, 405: S23-S26 (2010).
Mulliken, "Molecular Compounds and their Spectra. II." Journal of American Chemical Society, 74: 811-824 (1952).
Shirakawa et al., "Synthesis of Electrically Conducting Organic Polymers: Halogen Derivatives of Polyacetylene, (CH) x," J.C.S. Chem. Comm., 578-580, (1977).
Terauchi et al., "Protonic defect induced carrier doping in TTFCOO-NH4+: Tunable doping level by solvent," Synthetic Metals, 162: 531-535 (2012).
Terauchi et al., "Synthesis of bis-fued tetrathiafulvalene with mono- and dicarboxylic acids," Tetrahedron Letters, 53: 3277-3280 (2012).
Walzer et al., "Highly Efficient Organic Devices Based on Electrically Doped Transport Layers," Chem Rev 107: 1233-1271 (2007).
Terauchi et al., "Development of a novel salt-bridge molecular conductor composed of bis TTF-fused donor," 92nd Annual Meeting of the Chemical Society of Japan, Preprint IV, Mar. 9, 2012, p. 1642 (2PA-118).
Batail, ed. "Chemical Reviews," 104: 4887-5782 (2004).
International Search Report issued in corresponding International Patent Application No. PCT/JP2013/069451 dated Oct. 1, 2013.
Partial supplementary European search report dated Feb. 3, 2015, for European Application No. 13845891.4.

(Continued)

*Primary Examiner* — Taofiq A Solola
(74) *Attorney, Agent, or Firm* — Morgan, Lewis & Bockius LLP

(57) ABSTRACT

Provided are a compound capable of becoming an organic transparent electrode, etc. One aspect of the present invention relates to an organic transparent electrode, which is configured from an organic molecule having a Brønsted acid functional group, electron-donating properties, and a π-conjugated plane, characterized by being self-assembled. Another aspect of the present invention relates to the organic transparent electrode characterized in that the Brønsted acid functional group is one member selected from among a carboxylic acid functional group, a sulfonic acid functional group, a phosphonic acid functional group and a thiophosphonic acid functional group.

6 Claims, 12 Drawing Sheets

(56) References Cited

OTHER PUBLICATIONS

Furukawa et al., "Magnetic Resonance Investigations of Electronic States of TTPCOO Derivatives", Meeting Abstracts of the Physical Society of Japan, Aug. 24, 2012, vol. 67, Issue 2, (2012 Autumn Meeting) Part 4, p. 801 (21aEB-7).

Yang et al., "A New ex-TTF-Based Organogelator: Formulation of Organogels and Tuning with Fullerene", Langmuir, 2010, 26(14), pp. 11720-11725.

Japanese Office Action dated Mar. 2, 2015, for corresponding patent application No. JP 2014-511666.

* cited by examiner

HYDROGEN BOND NETWORK

ORGANIC TRANSPARENT ELECTRODE, METHOD FOR PRODUCING ORGANIC TRANSPARENT ELECTRODE, TOUCH PANEL, DISPLAY, ORGANIC METAL, METHOD FOR PRODUCING ORGANIC METAL, COMPOUND OR SALT THEREOF, ELECTRIC WIRE AND ELECTRONIC DEVICE

TECHNICAL FIELD

The present invention relates to an organic transparent electrode or a synthetic metal.

BACKGROUND ART

Transparent electrodes such as indium tin oxide (ITO) electrodes, for example, are very useful materials that are used in electronic devices, such as in mobile telephone displays. However, indium, which is the central element, is a rare metal whose price has recently increased dramatically. Considering future demand, it is desirable to replace indium with another, less expensive substance. To obtain a metal (synthetic metal) from typical elements such as carbon, nitrogen, oxygen, hydrogen, and sulfur atoms, there are two types of method, i.e., a method carried out with a charge transfer complex using an electrolytic oxidation method, and a method carried out with a conductive polymer by a chemical doping method that adds a doping agent.

Conventionally, it has not been possible to obtain an organic transparent electrode other than by these methods.

SUMMARY OF INVENTION

Technical Problem

It is an object of the present invention, which was created in view of the above-described background art, to provide a compound capable of becoming an organic transparent electrode, a compound capable of becoming an organic transparent electrode and the like.

Solution to Problem

According to the present invention, the configurations as described in the claims are employed in order to achieve the above-described objects. This invention will now be described in more detail.

A first aspect of the present invention is an organic transparent electrode characterized by being formed from an organic molecule having a Brønsted acid functional group, an electron-donating ability, and a π-conjugated plane, and being self-assembling.

A second aspect of the present invention is the organic transparent electrode according to claim 1, characterized in that the Brønsted acid functional group is any of a carboxylic acid functional group, a sulfonic acid functional group, a phosphonic acid functional group, and a thiophosphonic acid functional group.

A third aspect of the present invention is the organic transparent electrode according to claim 2, characterized in that a hydrogen bond is formed to the Brønsted acid functional group in a self-assembled state.

A fourth aspect of the present invention is an organic transparent electrode characterized by being formed from a compound that comprises a fused tetrathiafulvalene derivative moiety in a skeleton and has a protonic acid functional group.

A fifth aspect of the present invention is an organic transparent electrode characterized by being formed from any of the compounds represented by the following general formulae, wherein $R_1$, $R_2$, $R_3$, $R_4$, and R' may be the same or different, or a salt thereof.

[Formula 4]

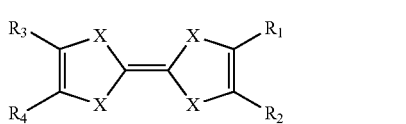 Pattern 1  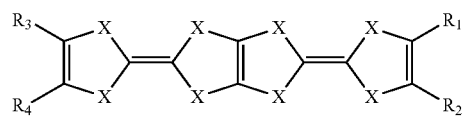 Pattern 2

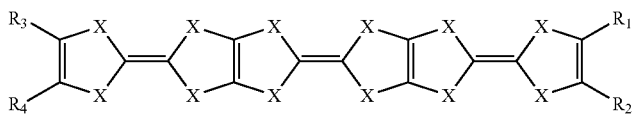 Pattern 3

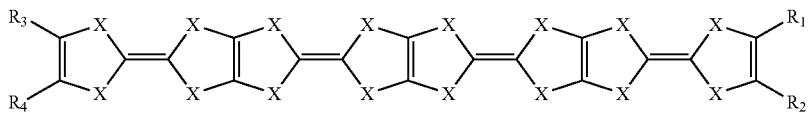 Pattern 4 wherein

X is selected from the group consisting of S, O, and Se;

$R_1$ and $R_2$ are independently selected from the group consisting of H, COOH, $SO_3H$, P(=O)OWOH, in which W is selected from the group consisting of H, Me, Et, Pr, and Bu, CnHm, in which n is from 1 to 30, and m is from 3 to 61, QCnHm, in which Q is selected from the group consisting of O, S, and Se, n is from 1 to 30, and m is from 3 to 61,

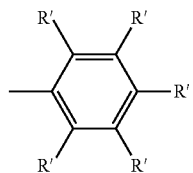

(R'=H, or QCnHm, in which Q is selected from the group consisting of O, S, and Se, n is from 1 to 30, and m is from 3 to 61),

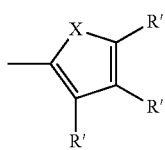

(R'=H, or QCnHm, in which Q is selected from the group consisting of O, S, and Se, n is from 1 to 30, and m is from 3 to 61), and

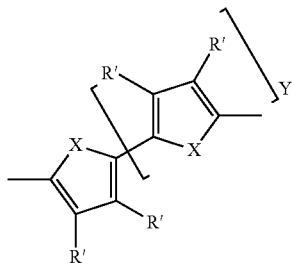

(R'=H, or QCnHm, in which Q is selected from the group consisting of O, S, and Se, n is from 1 to 30, m is from 3 to 61, and Y is from 1 to 50), or alternatively $R_1$ and $R_2$ are taken together to form —CnHm-, in which n is from 1 to 30, and m is from 3 to 61, -QCnHmQ-, -QCnHm-, in which Q is selected from the group consisting of O, S, and Se, n is from 1 to 30, and m is from 3 to 61, or -[Q(CnHm)i]j-, in which Q is selected from the group consisting of O, S, and Se, n is from 1 to 30, m is from 3 to 61, i is from 1 to 30, and j is from 1 to 30; and $R_3$ and $R_4$ are independently selected from the group consisting of H, COOH, SO$_3$H, P(=O)OWOH, in which W is selected from the group consisting of H, Me, Et, Pr, and Bu, CnHm, in which n is from 1 to 30, and m is from 3 to 61, QCnHm, in which Q is selected from the group consisting of O, S, and Se, n is from 1 to 30, and m is from 3 to 61,

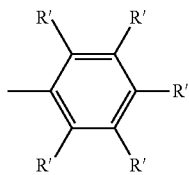

(R'=H, or QCnHm, in which Q is selected from the group consisting of O, S, and Se, n is from 1 to 30, and m is from 3 to 61),

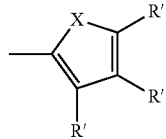

(R'=H, or QCnHm, in which Q is selected from the group consisting of O, S, and Se, n is from 1 to 30, and m is from 3 to 61), and

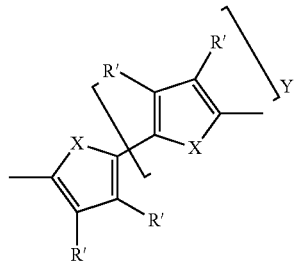

(R'=H, or QCnHm, in which Q is selected from the group consisting of O, S, and Se, n is from 1 to 30, m is from 3 to 61, and Y is from 1 to 50), or alternatively $R_3$ and $R_4$ are taken together to form —CnHm-, in which n is from 1 to 30, and m is from 3 to 61, -QCnHmQ-, -QCnHm-, in which Q is selected from the group consisting of O, S, and Se, n is from 1 to 30, and m is from 3 to 61, or -[Q(CnHm)i]j-, in which Q is selected from the group consisting of O, S, and Se, n is from 1 to 30, m is from 3 to 61, i is from 1 to 30, and j is from 1 to 30.

A sixth aspect of the present invention is an organic transparent electrode characterized by being formed from any of the compounds represented by the following general formulae, wherein $R_1$, $R_2$, $R_3$, $R_4$, and R' may be the same or different, or a salt thereof.

[Formula 8]

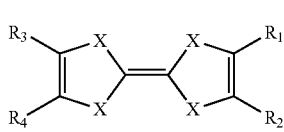

Pattern 1

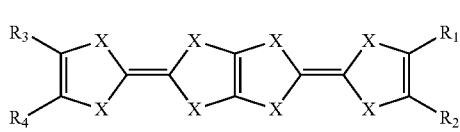

Pattern 2

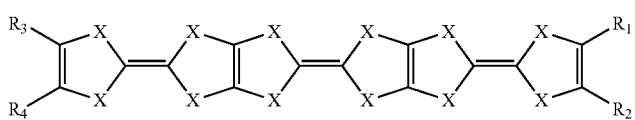

Pattern 3

-continued

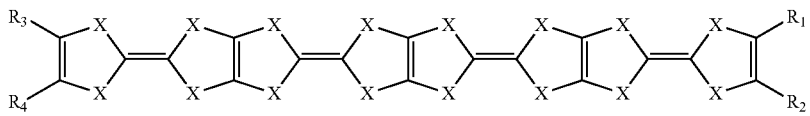

Pattern 4 wherein

X is selected from the group consisting of S, O, and Se;

$R_1$ and $R_2$ are independently selected from the group consisting of H, $COONH_4$, $COONH_3OH$, $COONH_3Z$, $SO_3NH_4$, $SO_3NH_3OH$, $SO_3NH_3Z$, $P(=O)OWONH_4$, in which W is selected from the group consisting of H, Me, Et, Pr, and Bu, $P(=O)OWONH_3OH$, in which W is selected from the group consisting of H, Me, Et, Pr, and Bu, $P(=O)OWONH_3Z$, in which W is selected from the group consisting of H, Me, Et, Pr, and Bu, and Z is Ph, or Ar, $NH_3A$, in which A is selected from the group consisting of F, Cl, Br, I, and $BF_4$, CH(W)$NH_3A$, in which W is selected from the group consisting of H, Me, Et, Pr, and Bu, and A is selected from the group consisting of F, Cl, Br, I, and $BF_4$, QCnHm, in which Q is selected from the group consisting of O, S, and Se, n is from 1 to 30, and m is from 3 to 61,

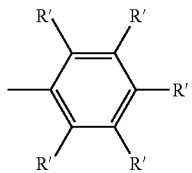

(R'=H, or QCnHm, in which Q is selected from the group consisting of O, S, and Se, n is from 1 to 30, and m is from 3 to 61),

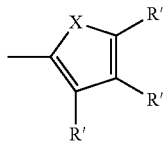

(R'=H, or QCnHm, in which Q is selected from the group consisting of O, S, and Se, n is from 1 to 30, and m is from 3 to 61), and

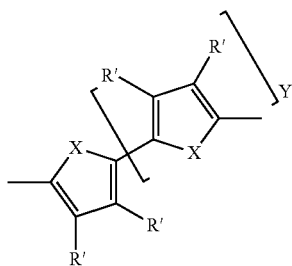

(R'=H, or QCnHm, in which Q is selected from the group consisting of O, S, and Se, n is from 1 to 30, m is from 3 to 61, and Y is from 1 to 50), or alternatively $R_1$ and $R_2$ are taken together to form —CnHm-, in which n is from 1 to 30, and m is from 3 to 61, -QCnHmQ-, -QCnHm-, in which Q is selected from the group consisting of O, S, and Se, n is from 1 to 30, and m is from 3 to 61, or -[Q(CnHm)i]j-, in which Q is selected from the group consisting of O, S, and Se, n is from 1 to 30, m is from 3 to 61, i is from 1 to 30, and j is from 1 to 30; and $R_3$ and $R_4$ are independently selected from the group consisting of H, $COONH_4$, $COONH_3OH$, $COONH_3Z$, $SO_3NH_4$, $SO_3NH_3OH$, $SO_3NH_3Z$, $P(=O)OWONH_4$, in which W is selected from the group consisting of H, Me, Et, Pr, and Bu, $P(=O)OWONH_3OH$, in which W is selected from the group consisting of H, Me, Et, Pr, and Bu, $P(=O)OWONH_3Z$, in which W is selected from the group consisting of H, Me, Et, Pr, and Bu, and Z is Ph, or Ar, $NH_3A$, in which A is selected from the group consisting of F, Cl, Br, I, and $BF_4$, CH(W)$NH_3A$, in which W is selected from the group consisting of H, Me, Et, Pr, and Bu, and A is selected from the group consisting of F, Cl, Br, I, and $BF_4$, QCnHm, in which Q is selected from the group consisting of O, S, and Se, n is from 1 to 30, and m is from 3 to 61,

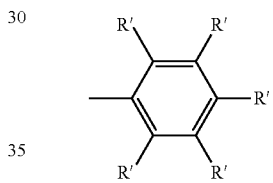

(R'=H, or QCnHm, in which Q is selected from the group consisting of O, S, and Se, n is from 1 to 30, and m is from 3 to 61),

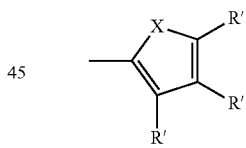

(R'=H, or QCnHm, in which Q is selected from the group consisting of O, S, and Se, n is from 1 to 30, and m is from 3 to 61), and

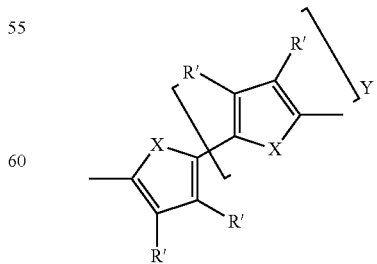

(R'=H, or QCnHm, in which Q is selected from the group consisting of O, S, and Se, n is from 1 to 30, m is from 3 to 61, and Y is from 1 to 50), or alternatively $R_3$ and $R_4$ are taken together to form —CnHm-, in which n is from 1 to 30, and m is from 3 to 61, -QCnHmQ-, -QCnHm-, in which Q is selected from the group consisting of O, S, and Se, n is from 1 to 30, and m is from 3 to 61, or -[Q(CnHm)i]j-, in which Q is selected from the group consisting of O, S, and Se, n is from 1 to 30, m is from 3 to 61, i is from 1 to 30, and j is from 1 to 30.

A seventh aspect of the present invention is an organic transparent electrode characterized by being formed from a compound represented by Formula 1 or a salt thereof

[Formula 1]

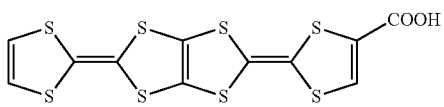

1

An eighth aspect of the present invention is an organic transparent electrode characterized by being formed from a compound represented by Formula 2 or a salt thereof.

[Formula 2]

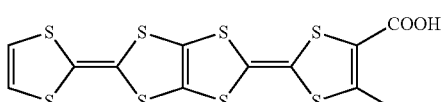

2

A ninth aspect of the present invention is an organic transparent electrode characterized by being formed from a compound represented by Formula 3 or a salt thereof.

[Formula 3]

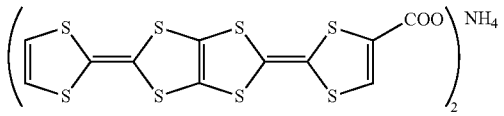

3

A tenth aspect of the present invention is an organic transparent electrode characterized by being formed from an anilinium tetrathiafulvalene-2-carboxylate salt.

An eleventh aspect of the present invention is an organic transparent electrode characterized by being formed from a hydroxyammonium tetrathiafulvalene-2-carboxylate salt.

A twelfth aspect of the present invention is an organic transparent electrode characterized by being formed from a compound represented by the following formula: $[(TTP\text{-}COO^-NH_4^+)(TTPCOOH)]_{1-x}(TTP^{\cdot+}COO^-NH_3)_x$, wherein x is 0.06.

[Formula 12]

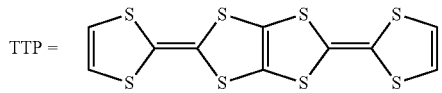

A thirteenth aspect of the present invention is a method for producing an organic transparent electrode, comprising recrystallizing from an organic solvent a fused sulfur-containing π compound to which a carboxylic acid functional group has been introduced.

A fourteenth aspect of the present invention is a method for producing an organic transparent electrode, comprising recrystallizing a fused tetrathiafulvalene to which a carboxylic acid functional group has been introduced, from an organic solvent to which an ammonia solution has been added.

A fifteenth aspect of the present invention is a touch panel comprising the organic transparent electrode described herein.

A sixteenth aspect of the present invention is a display comprising the organic transparent electrode described herein.

A seventeenth aspect of the present invention is an electronic device comprising the organic transparent electrode described herein.

An eighteenth aspect of the present invention is an organic transparent electrode comprising an organic compound having protonic defects in a hydrogen bond network, wherein a radical cation or a radical anion is generated to replenish a lost charge.

A nineteenth aspect of the present invention is an organic transparent electrode wherein charges are not in equilibrium due to a ratio of a cation and an anion present in a hydrogen bond network not being 1:1, and a radical cation or a radical anion is generated to replenish a lost charge.

A twentieth aspect of the present invention is a synthetic metal characterized by being formed from an organic molecule having a Brønsted acid functional group, an electron-donating ability, and a π-conjugated plane, and being self-assembling.

A twenty-first aspect of the present invention is the synthetic metal described herein, characterized in that the Brønsted acid functional group is any of a carboxylic acid functional group, a sulfonic acid functional group, a phosphonic acid functional group, and a thiophosphonic acid functional group.

A twenty-second aspect of the present invention is the synthetic metal described herein, characterized in that a hydrogen bond is formed to the Brønsted acid functional group in a self-assembled state.

A twenty-third aspect of the present invention is a synthetic metal characterized by being formed from a compound that comprises a fused tetrathiafulvalene derivative moiety in a skeleton and has a protonic acid functional group.

A twenty-fourth aspect of the present invention is a synthetic metal characterized by being any of the compounds represented by Formula 4A, wherein $R_1$, $R_2$, $R_3$, and $R_4$ may be the same or different, or a salt thereof.

[Formula 4A]

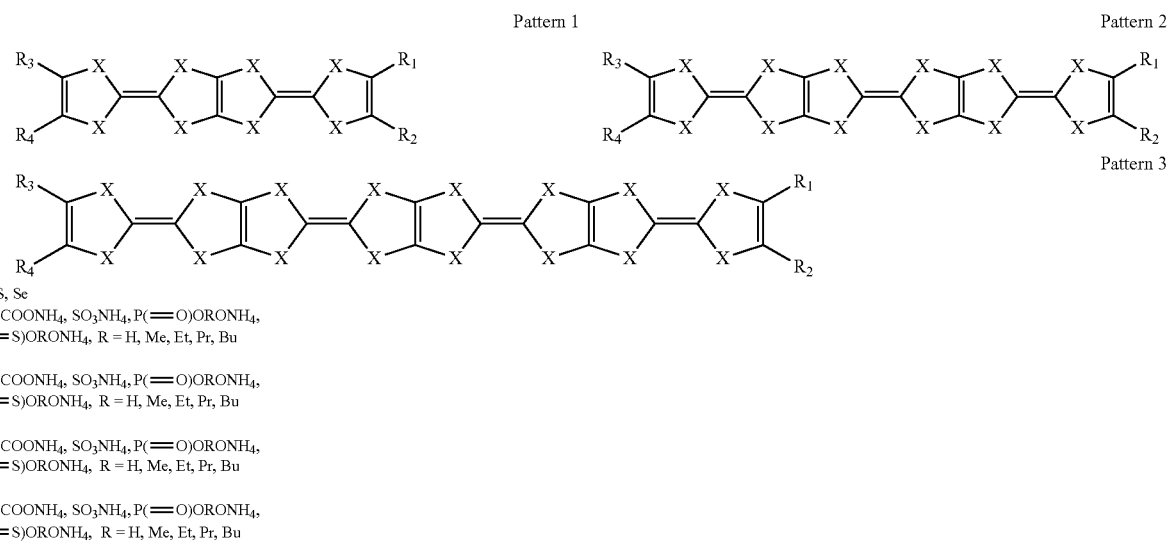

X = S, Se
R$_1$ = COONH$_4$, SO$_3$NH$_4$, P(=O)ORONH$_4$,
P(=S)ORONH$_4$, R = H, Me, Et, Pr, Bu

R$_2$ = COONH$_4$, SO$_3$NH$_4$, P(=O)ORONH$_4$,
P(=S)ORONH$_4$, R = H, Me, Et, Pr, Bu

R$_3$ = COONH$_4$, SO$_3$NH$_4$, P(=O)ORONH$_4$,
P(=S)ORONH$_4$, R = H, Me, Et, Pr, Bu

R$_4$ = COONH$_4$, SO$_3$NH$_4$, P(=O)ORONH$_4$,
P(=S)ORONH$_4$, R = H, Me, Et, Pr, Bu

A twenty-fifth aspect of the present invention is a synthetic metal that is any of the compounds represented by Formula 5A, wherein R$_1$, R$_2$, R$_3$, and R$_4$ may be the same or different, or a salt thereof.

[Formula 5A]

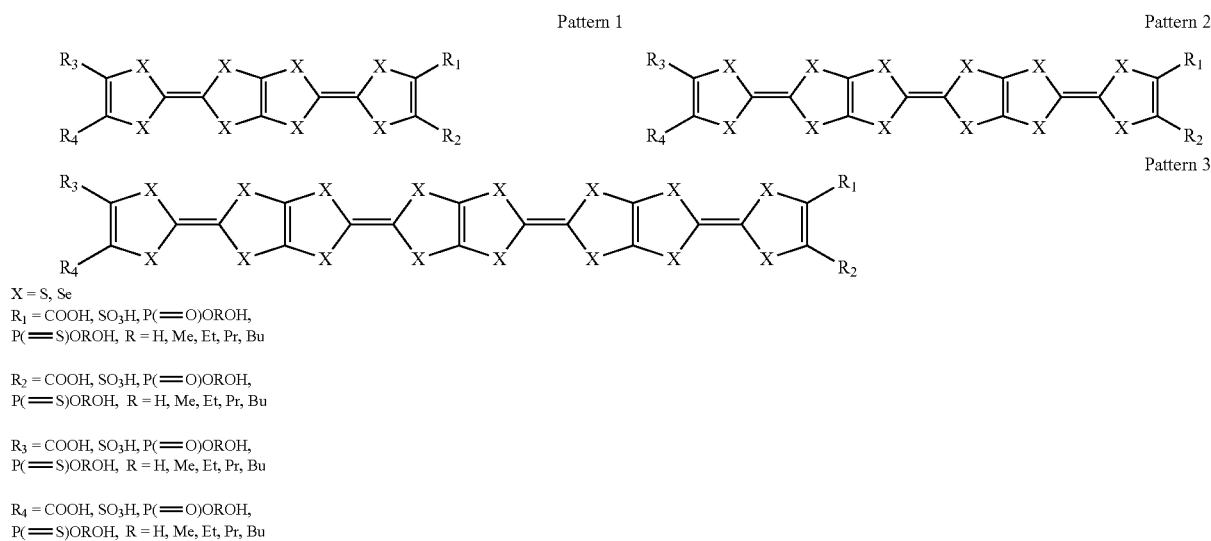

X = S, Se
R$_1$ = COOH, SO$_3$H, P(=O)OROH,
P(=S)OROH, R = H, Me, Et, Pr, Bu

R$_2$ = COOH, SO$_3$H, P(=O)OROH,
P(=S)OROH, R = H, Me, Et, Pr, Bu

R$_3$ = COOH, SO$_3$H, P(=O)OROH,
P(=S)OROH, R = H, Me, Et, Pr, Bu

R$_4$ = COOH, SO$_3$H, P(=O)OROH,
P(=S)OROH, R = H, Me, Et, Pr, Bu

A twenty-sixth aspect of the present invention is a compound represented by Formula 1A or a salt thereof.

A twenty-seventh aspect of the present invention is a compound represented by Formula 2A or a salt thereof.

[Formula 1A]

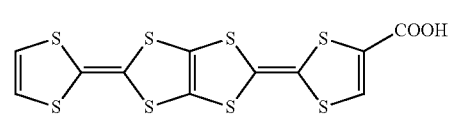

[Formula 2A]

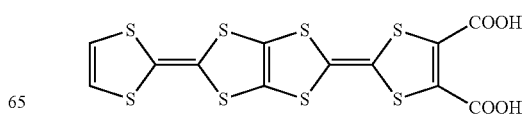

A twenty-eighth aspect of the present invention is a compound represented by Formula 3A or a salt thereof.

[Formula 3A]

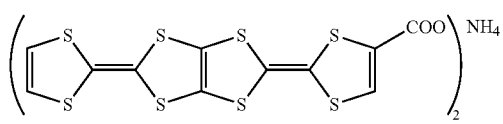

A twenty-ninth aspect of the present invention is a synthetic metal characterized by being a compound represented by Formula 1A or a salt thereof.

[Formula 1A]

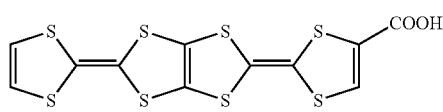

A thirtieth aspect of the present invention is a synthetic metal characterized by being a compound represented by Formula 2A or a salt thereof.

[Formula 2A]

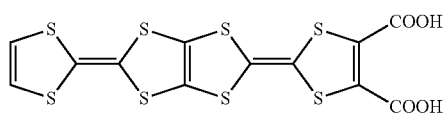

A thirty-first aspect of the present invention is a synthetic metal characterized by being a compound represented by Formula 3A or a salt thereof.

[Formula 3A]

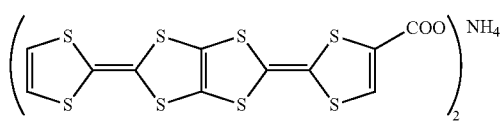

A thirty-second aspect of the present invention is a synthetic metal characterized by being a compound represented by the following formula: $[(TTPCOO^-NH_4^+)(TTP\text{-}COOH)]_{1-x}(TTP.^+COO^-NH_3)_x$, wherein x is 0.06.

[Formula 6A]

TTP = 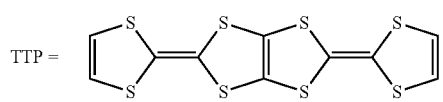

A thirty-third aspect of the present invention is a method for producing a synthetic metal, comprising recrystallizing from an organic solvent a fused sulfur-containing π compound to which a carboxylic acid functional group has been introduced.

A thirty-fourth aspect of the present invention is a method for producing a synthetic metal, comprising recrystallizing a fused tetrathiafulvalene to which a carboxylic acid functional group has been introduced from an organic solvent to which an ammonia solution has been added.

A thirty-fifth aspect of the present invention is a wire comprising the synthetic metal described herein.

A thirty-sixth aspect of the present invention is an electronic device comprising the synthetic metal described herein.

A thirty-seventh aspect of the present invention is a synthetic metal comprising an organic compound having a proton defect in a hydrogen bond network, wherein a radical cation or a radical anion is generated to replenish a lost charge.

A thirty-eighth aspect of the present invention is a synthetic metal wherein charges are not in equilibrium due to a ratio of a cation and an anion present in a hydrogen bond network not being 1:1, and a radical cation or a radical anion is generated to replenish a lost charge.

Examples of the Brønsted acid functional group include —COOH, —SO$_3$H, and —P(=X)OROH (X=O or S, R=H, Me, Et, Pr, Bu). A primary amine is represented by —NH$_n$D$_{3-n}$ (n=2 to 0, and D is deuterium), for example. Further, examples of inorganic acids include HBF$_4$, HClO$_4$, HCl, HBr, HI, DBF$_4$, DClO$_4$, DCl, DBr, and DI. Examples of inorganic bases include NH$_n$D$_{3-n}$ (n=3 to 0), NH$_n$D$_{2-n}$OH (n=2 to 0), and NH$_n$D$_{2-n}$OD (n=2 to 0).

Further, the term "metal" refers to a conductor through which electricity passes well. For example, at around room temperature, the electrical conductivity of a pressure-formed pellet is greater than about 1 S/cm. The term "transparent" refers to, for example, a transmittance of around 80% or more over a wide wavelength region (e.g.: 500 to 2000 nm). An electrode is a material having a conductivity of around 0.0001 S/cm or more at around room temperature, for example.

The term "donor" refers to an electron donator, i.e., an electron donating molecule or an electron donating group. Further, the term "acceptor" refers to an electron acceptor, i.e., an electron accepting molecule or an electron accepting group.

The term "room temperature" refers to a temperature of 300 K (27° C.), and the term "around room temperature" means that room temperature±about 10° C.

Further, the compounds in the specification and the claims include compounds having an equivalent structure in which an element is substituted with an elemental isotope, such as deuterium.

Advantageous Effects of Invention

According to the present invention, a compound or the like is obtained that is capable of forming an organic transparent electrode or a synthetic metal. Further objectives, characteristics, and advantages of the present invention will become apparent from the detailed description that is based on the following embodiments of the present invention and the attached drawings.

DESCRIPTION OF EMBODIMENTS

Figure 1:
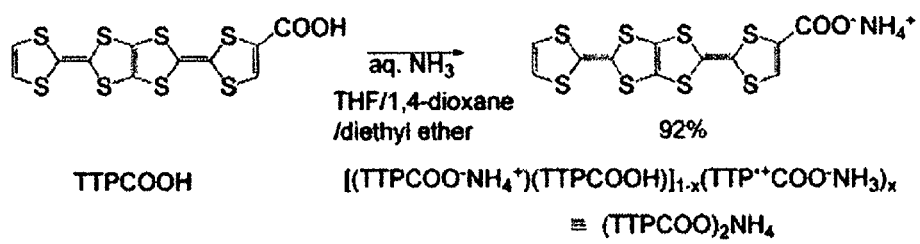
FIG. 1 is a diagram illustrating a synthesis scheme.

Embodiments of the present invention will now be described in more detail with reference to the drawings.

[Outline]

The present embodiment relates to a method and the like for producing an electrode material having a high transmittance from an organic substance that is formed only from typical elements without using rare metals. Organic substances have large industrial advantages, since their raw materials are not only inexpensive, but also organic substances are light and flexible. According to the present method, an organic transparent electrode can be obtained just by metallizing.

Further, the compound according to the present embodiment has a high transmittance to light across a wide wavelength range.

Although the material of the organic transparent electrode is not necessarily limited to a synthetic metal, if the material is a synthetic metal, the electrode can be used as an organic transparent electrode. Therefore, a method for producing a synthetic metal will be described below in more detail.

The present embodiment uses a new production method for synthesizing a synthetic metal without employing an electrolytic oxidation method or a chemical doping method. According to the method, a metallized organic substance can be obtained simply by introducing a carboxylic acid functional group into a fused sulfur-containing π compound (fused tetrathiafulvalene) and recrystallizing from an organic solvent to which an ammonia solution has been added.

This production method makes it possible to obtain a large amount of a stable synthetic metal easily at a time, since this method not only makes a large-scale apparatus for electrolytic oxidation unnecessary, but also avoids the degradation and instability of the substances that are produced during chemical doping. Accordingly, this method is a revolutionary production method that enables production of large amounts of a synthetic metal on an industrial scale. Consequently, this method will greatly broaden the possibilities of organic materials as a substitute substance for metal resources.

Specifically, the present inventors synthesized an organic ammonium salt having a high conductivity without electrolytic oxidation or addition of a dopant. Based on electron transportation and spectroanalysis, this salt acts as a metal until at least 4 K, has a magnetic susceptibility at room temperature that is ten-times higher than a typical charge transfer complex, and exhibits an antiferromagnetic behavior at 25 K or less.

[History of the Invention]

Synthetic metals formed purely from light elements are attracting a lot of attention both academically and industrially. However, considering industrial-scale applications, it is desirable to synthesize a synthetic metal without electrolytic oxidation.

Non Patent Literature 1: (a) Mulliken, R. S. J. Am. Chem. Soc. 1952, 74, 811-824.

Non Patent Literature 2: (b) Akamatsu, H.; Inokuchi, H.; Matsunaga, Y. Nature 1954, 4395, 168-169.

Non Patent Literature 3: (c) Shirakawa, H.; Louis, E. J.; MacDiarmid, A. G.; Chiang, C. K.; Heeger, A. J. J. Chem. Soc., Chem. Commun 1977, 578.

Non Patent Literature 4: (d) Batail, P. Ed. Chem. Rev. 2004, 104, 11 (special issue for molecular conductors), 4887-5782.

Non Patent Literature 5: (e) Walzer K.; Maennig, B.; Pfeiffer M.; Leo, K. Chem. Rev. 2007, 107, 1233-1271.

Non Patent Literature 6: (f) Kirtley, J. R.; Mann-hart, J. Nature Mat. 2008, 7, 520-521.

The present inventors have recently found that an ammonium salt co-existing with a certain electron donor molecule is spontaneously doped, thereby generating hole carriers at the ammonium salt forming stage.

Non Patent Literature 7: (a) Kobayashi, Y.; Yoshioka, M.; Saigo, K.; Hashizume, D.; Ogura, T. J. Am. Chem. Soc. 2009, 131, 9997-10002.

Non Patent Literature 8: (b) Kobayashi, Y.; Yoshioka, M.; Saigo, K.; Hashizume, D.; Ogura, T. Physica B 2010, 405, S23-S26.

Non Patent Literature 9: (c) Kobayashi, Y.; Suzuki, A.; Yamada, Y.; Saigo, K.; Shibue, T. Syn. Met. 2010, 160, 575-583, Non Patent Literature 10: (d) Furukawa, K.; Nakamura, T.; Kobayashi, Y.; Ogura, T. J. Phys. Soc. Jpn. 2010, 79, 053701-4.

Non Patent Literature 11: (e) Terauchi, T.; Kobayashi, Y.; Iwai, H.; Tanaka, A. Syn. Met. 2012, 162, 531-535.

In this doping method, charge neutrality is ensured by having a partial proton deficit in the ammonium ion moiety, instead of adding a dopant in the same way as the conventional conductive polymers. The tetrathiafulvalene carboxylic acid ammonium salt $(TTFCOO^-NH_4^+)_{1-x}(TTF.^+COO^-NH_3)_x$, wherein x is 0.16 (herein abbreviated as $TTFCOONH_4$), is the first reported hole-doped semiconductor, on which the carrier generation mechanism and the source for exhibiting conductivity, etc. have been explained. Further, just recently, a single crystal of tetrathiafulvalene carboxylic acid anilinium salt was obtained, from which it was clear that this doping phenomenon was not just due to surface effects, but a bulk property of the substance. These facts illustrate the high likelihood that a "charge deficit" dopant will create a new synthetic metal without the use of electrolytic oxidation.

The present inventors designed tetrathiapentalene (fused tetrathiafulvalene) carboxylic acid ammonium salt $(TTPCOO)_2NH_4$ as a novel molecule, which is intended to widen the band width of the valence band by expanding the overlap in the π orbital.

[Physical Properties and the Like of Compound]

Specific compounds will be mentioned below and described in more detail for their physical properties and the like.

FIG. 1 is a diagram illustrating a synthesis scheme. The precursor TTPCOOH was synthesized without using a metal catalyst even once at any stage of the synthesis pathway. A salt is obtained as a black-brown solid in a yield of 92% by recrystallizing an ammonium salt of TTPCOOH from an aqueous ammonia solution of TTPCOOH with an organic solvent (THF/1,4-dioxane/diethyl ether).

The composition has a 2:1 ratio of acid:base. It was confirmed based on the $^1$H-NMR spectrum that all of the TTP-COOH was converted into the ammonium salt. Measurement of the N (1s) core level of this salt by X-ray photoemission spectroscopy showed that the salt had peaks at 401.3 eV and 399.6 eV, which were identified as ammonium ions and ammonia, respectively. Since the ammonia is about 6%, the correct formula is $[(TTPCOO^-NH_4^+)(TTPCOOH)]_{1-x}(TTP.^+COO^-NH_3)_x$, wherein x is 0.06. On the other hand, the ESR spectrum shows a large radical spin density of 32%. This was identified from the g value of 2.00575 as coming from TTP radical cations.

Next, three fused tetrathiafulvalene derivatives synthesized by the present inventors will be shown.

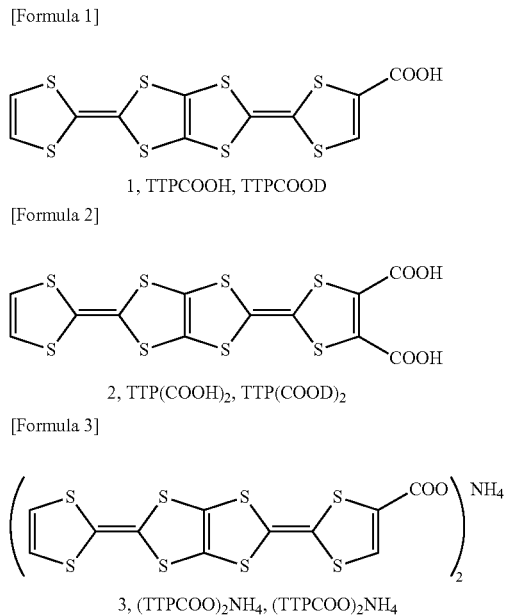

[Formula 1]

1, TTPCOOH, TTPCOOD

[Formula 2]

2, TTP(COOH)$_2$, TTP(COOD)$_2$

[Formula 3]

3, (TTPCOO)$_2$NH$_4$, (TTPCOO)$_2$NH$_4$

Figure 2:
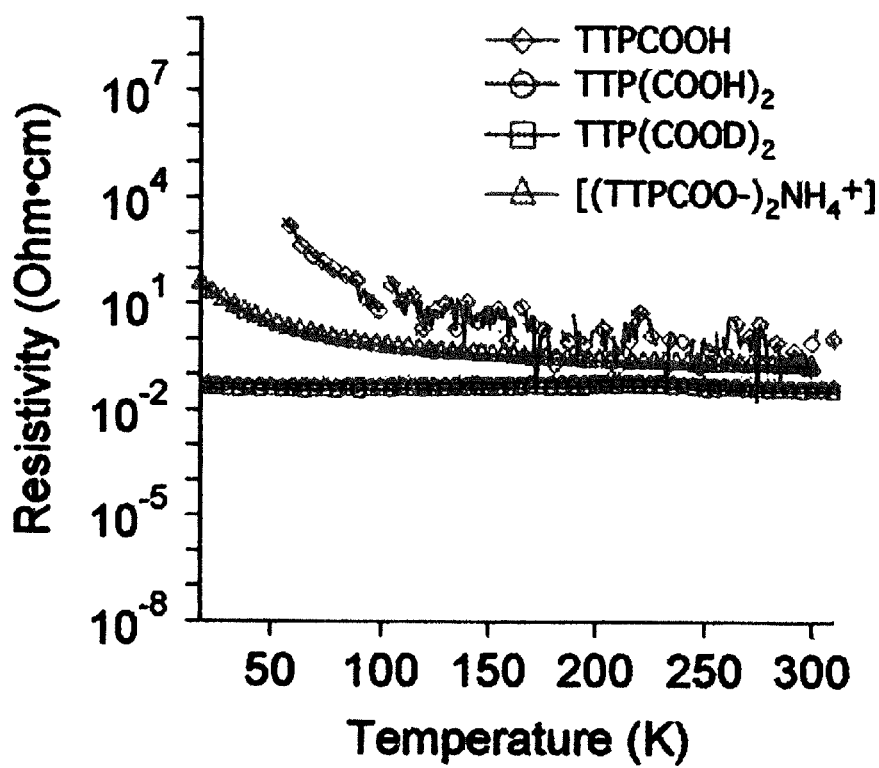
FIG. 2 is a diagram illustrating the temperature dependence of the electrical resistance of Formula 1, Formula 2, and Formula 3.

FIG. 2 is a diagram illustrating the temperature dependence of the electrical resistance of Formula 1, Formula 2, and Formula 3. Among these, for Formula 2 and Formula 3, it was confirmed that a pellet specimen formed by pressure-forming a powder was metallized. Since the deuterium-substituted specimen exhibits almost the same behavior, only the example of Formula 2 is shown.

Figure 3:
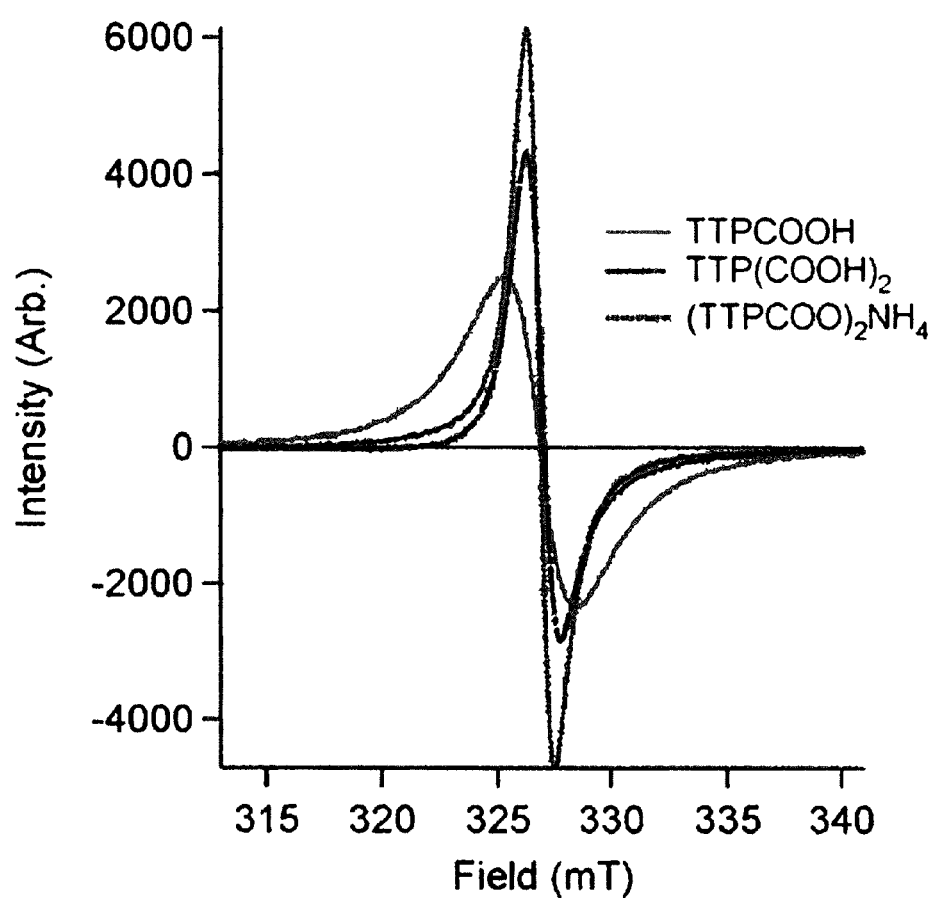
FIG. 3 is a diagram illustrating the ESR spectra at room temperature of Formula 1, Formula 2, and Formula 3.

FIG. 3 is a diagram illustrating the ESR spectra at room temperature of Formula 1, Formula 2, and Formula 3. The spin densities of Formula 1, Formula 2, and Formula 3 are determined as 37%, 32%, and 12%, respectively, by electron spin resonance (ESR) at room temperature based on the standard substance DPPH.

Figure 4:
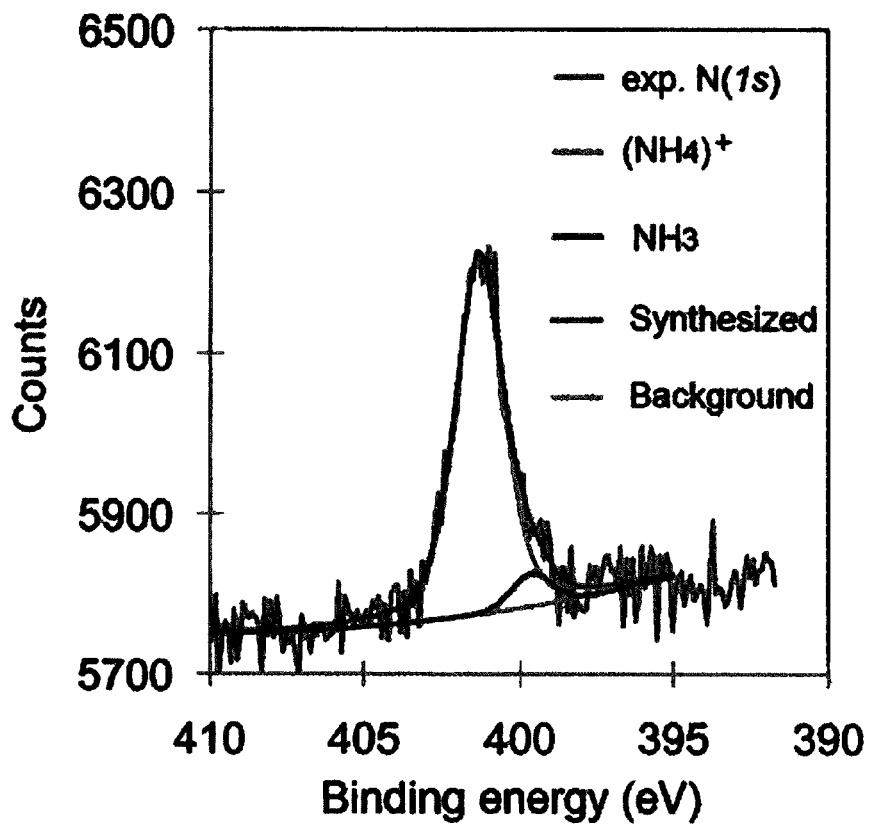
FIG. 4 is a diagram illustrating the XPS spectra at room temperature of the nitrogen atom inner-shell level (1s) of Formula 3.

FIG. 4 is a diagram illustrating the XPS spectra at room temperature of nitrogen atom N 1s core level of Formula 3. The source of metallization is attributed to self doping for replenishing the lost charges from proton defects that occur in a salt bridge bond. This fact was confirmed by X-ray photoemission spectroscopy for Formula 3 (TTPCOO)$_2$NH$_4$.

In other words, FIG. 4 illustrates the bond energy of N 1s of Formula 3. The amount of proton defects in Formula 3, which is the most representative substance, can be estimated by photoemission spectroscopy (XPS) as being 6% from the mixed ratio of NH$_3$ species in the nitrogen is orbital. The presence of these proton defects causes molecular spin in the crystal.

Figure 5:
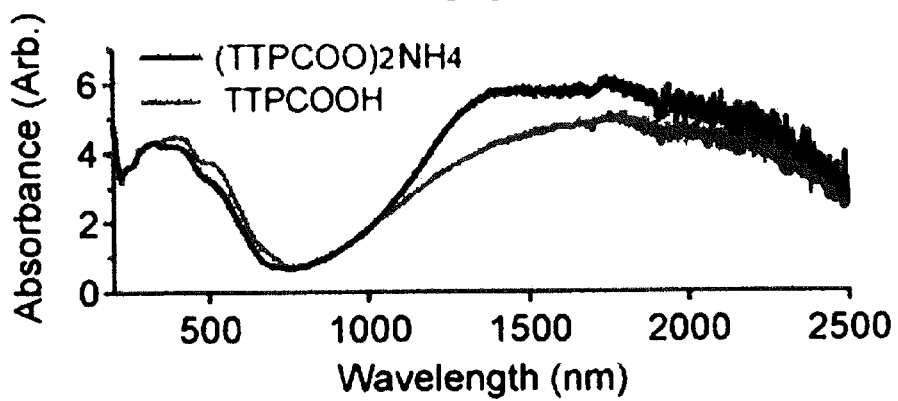
FIG. 5 is a diagram illustrating the normalized near-infrared absorption spectra of $(TTPCOO)_2NH_4$ and TTPCOOH.

FIG. 5 is a diagram illustrating the normalized near-infrared absorption spectra of (TTPCOO)$_2$NH$_4$ and TTPCOOH. Both of these substances exhibit a large absorption showing intermolecular transitions of the TTP moiety, which is in a mixed valence state at 800 nm or more. This is related to the delocalized amphoteric ion radical species $[(TTP)^{0.5+}]COO^-$ in the molecular arrangement, as both substances have a free carrier. It is thought that the self-protonated species TTPH$^+$COO$^-$, which is generated in TTPCOOH, replaces the role that was borne by the proton defects for the ammonium salt.

Figure 6:
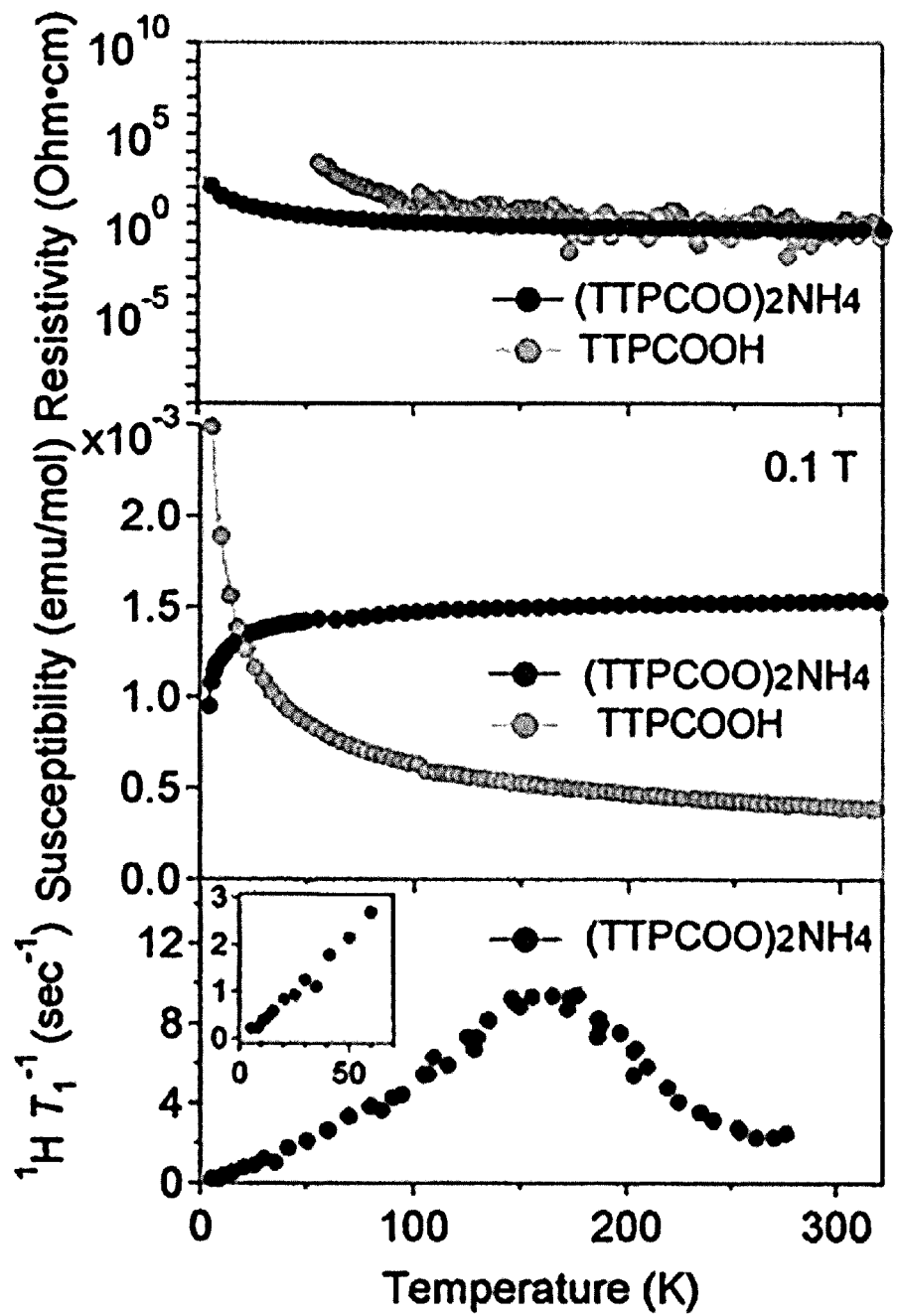
FIG. 6 is a diagram illustrating the electrical properties of $(TTPCOO)_2NH_4$ and TTPCOOH.

FIG. 6 is a diagram illustrating the electrical properties of (TTPCOO)$_2$NH$_4$ and TTPCOOH. Electrical resistance was measured using a pressure-formed sample from 4 to 320 K by a four-terminal method using a gold paste for the contact terminals (FIG. 6a). The TTPCOOH resistance suddenly increases at 100 K or less, exhibiting a semiconductor-like nature. On the other hand, the (TTPCOO)$_2$NH$_4$ resistance value hardly changes over the measurement temperature range. The slight increase in the resistance value at 25 K or less is attributed to the increase in grain boundary resistance in the pellet sample. The direct current conductivity (dc conductivity) at room temperature is 2.3 S/cm for (TTPCOO)$_2$NH$_4$ and 1.2 S/cm for TTPCOOH. These conductivity values are four orders of magnitude greater than the TTFCOONH$_4$ pellet sample.

FIG. 6b illustrates the temperature dependence of magnetic susceptibility when a 0.1 T magnetic field is applied. The antiferromagnetic effect derived from the inner shell electrons of the organic substance has been subtracted. The absolute value of the magnetic susceptibility at room temperature is $4.0 \times 10^{-4}$ emu/mol for TTPCOOH and $1.5 \times 10^{-3}$ emu/mol for (TTPCOO)$_2$NH$_4$. The latter value is an order of magnitude greater than a typical charge transfer complex formed from a pure organic substance. In addition, (TTPCOO)$_2$NH$_4$ exhibits an antiferromagnetic behavior at 25 K or less. From broad-line solid-state $^1$H-NMR measurement, the temperature dependence of relaxation time of the nuclear spin of (TTPCOO)$_2$NH$_4$ is in line with $T_1^{-1}$, thus proving that the substance was metallized.

It is thought that the TTP skeleton tends to assemble two-dimensionally due to the expanded π-conjugated moiety of the TTP skeleton, which causes delocalization of the amphoteric ion radical species in the molecular arrangement, thereby enabling metallization.

Next, the outline of the molecular assembly structure and the like will be described.

Figure 7:
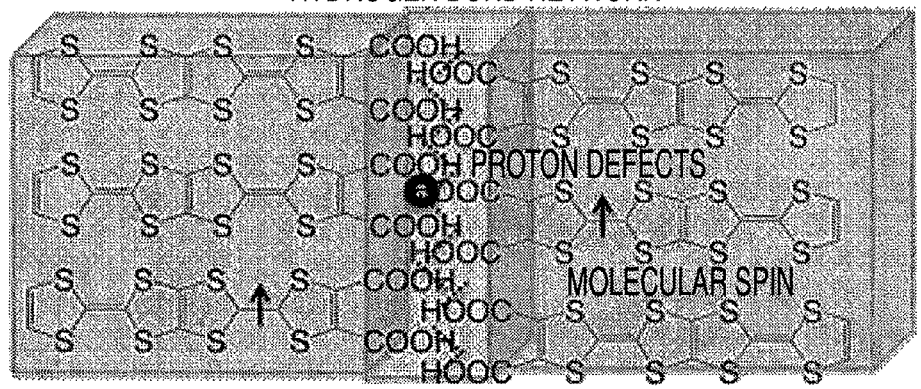
FIG. 7 is a schematic diagram illustrating a steric structure that focuses on intermolecular bonding and the interactions among molecules.

FIG. 7 is a schematic diagram illustrating a steric structure that focuses on intermolecular bonding and the interactions among molecules. As illustrated in the drawing, a hydrogen bond network is formed.

Regarding electrical conductivity, from the frequency dependence in the dielectric dispersion of the deuterium sample, it is clear that the hydrogen bonds are barely contributing to electrical conductivity.

Ammonium not only serves as the key for exhibiting the physical properties, but also plays a role in making the TTF (donor) molecules effectively self-assemble into a molecular arrangement that is suited to the carrier transport phenomenon.

These compounds are organic substances that are carrier-doped in order to replenish the lost charges of the proton defects mainly produced in the salt bridge bonds.

Organic radical species are highly reactive due to having a radical spin electron state that is in the HOMO level. Therefore, organic radical species exhibit a strong tendency to be degraded by external factors, such as oxygen in the air. Accordingly, to put an organic radical species in a chemically stable electron state, it is common to introduce an electron-withdrawing group, such as a cyano group or a nitro group, into the molecule to stabilize the species. Accordingly, the state in which radical spin has been produced by subjecting a radical species to measures to obtain an electron state such that the composition and electron state of the initially-synthesized molecules are retained and the radical species is not easily degraded even when stored for an extended period in air, is herein referred to as the "radical species is stably produced."

The d orbital of a transition metal element and the f orbital of a rare earth metal element are atomic orbitals that are positioned in a more inner shell than the s orbital and the p orbital of the outermost shell and have a high localization, and thus have a lower orbital energy. The electron state of the d orbital and the f orbital is called a quasi closed-shell configuration. In such a configuration, because of the high localization of these orbitals, the d electrons and the f electrons occupying these orbitals tend not to become involved in chemical bonding, so that odd electrons are stabilized. The nature of such odd electrons, which have a quasi closed-shell configuration, do not participate in chemical bonding, and are strongly stabilized, often becomes a cause of magnetism. The quasi closed-shell configuration will be described in more detail later.

Examples of preferred synthetic metals include the following.

(1) A salt bridge substance that has multiple bonds capable of being protonated in an electron donor or an electron acceptor molecule, in which 0.1% or more of a radical species based on the whole is stably produced during salt bridge formation. More preferred is a synthetic metal in which the radical spin electron state has a quasi closed-shell configuration.

The grounds for this are that, as confirmed experimentally, when radical spin is produced in a density of 0.1% or more, and that electron state is a quasi closed-shell configuration, the radical spin electrons act as free carriers, so that an electron conductivity of about $10^{-5}$ S/cm or more is exhibited.

(2) A substance that includes a hydrogen bond self-assembling moiety, in which 0.1% or more of a radical species based on the whole is stably produced by adding a Brønsted acid or base to a low-molecular weight organic compound having a molecular weight of 20,000 or less. More preferred is the substance in which the radical spin electron state has a quasi closed-shell configuration.

Even for a polymer, it is preferred to have a self-assembling site partially by the hydrogen bond functional groups. To achieve this, it is desirable for the molecular weight to be 20,000 or less. In order to sufficiently exhibit magnetic properties, it is desirable that the proton defects have been uniformly introduced throughout the substance, so that a uniform doping state can be obtained. If the molecular weight is extremely large, the difficulty level is likely to increase, so it is even more preferred that the molecular weight is 10,000 or less.

Next, the physical properties of the following two compounds will be described.

Compound A: Tetrathiafulvalene-2-carboxylic acid aniline salt single crystal (TTFCOONH$_3$Ph)
Compound B: Tetrathiafulvalene-2-carboxylic acid hydroxyamine salt single crystal (TTFCOONH$_3$OH)

Figure 13:
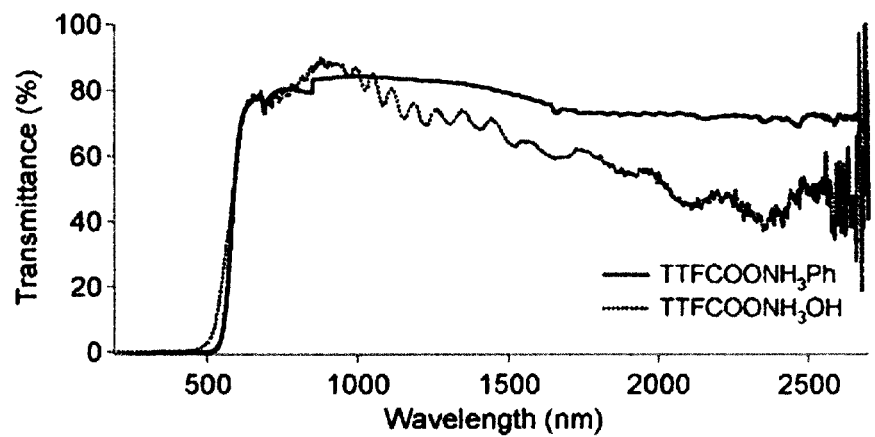
FIG. 13 is a diagram illustrating light transmittance in the ultraviolet/visible/near-infrared regions of Compound A and Compound B.

FIG. 13 is a diagram illustrating light transmittance in the ultraviolet/visible/near-infrared regions of Compound A and Compound B. According to the diagram, both compounds exhibit a high transmittance at about 500 nm or more, and a high transmittance exceeding 80% at 530 nm. Further, since transmittance of about 70% is exhibited from the visible to near-infrared region, the light transmittance is at a practical level.

Figure 14:
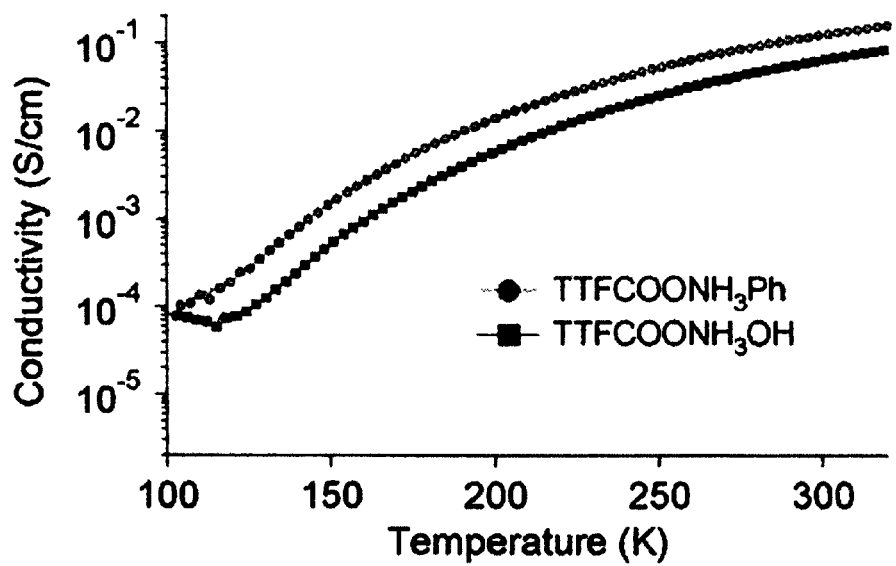
FIG. 14 is a diagram illustrating temperature dependence of electrical conductivity of Compound A and Compound B.

FIG. 14 is a diagram illustrating the temperature dependence of the electrical conductivity of Compound A and Compound B. According to the diagram, both compounds have an electrical conductivity of about 0.1 S/cm at room temperature. Both compounds exhibit a heat-activated type temperature dependence with a band gap of 0.11 eV (1) and 0.13 eV (2), respectively.

Next, the physical properties of the following compound will be described.

[Formula 2]

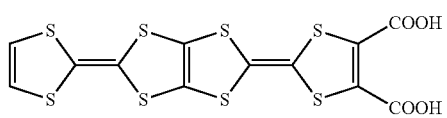

2

Figure 15:
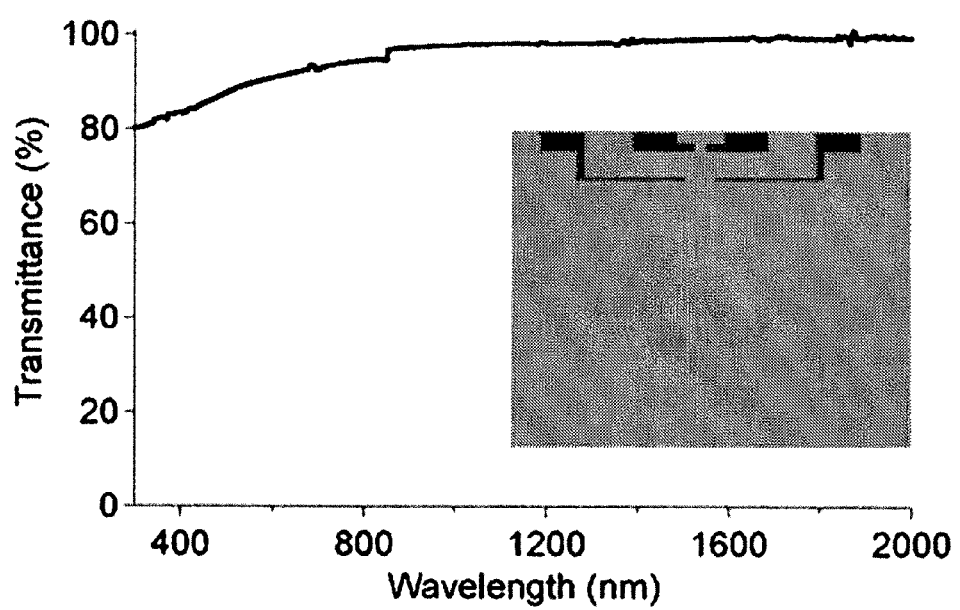
FIG. 15 is a diagram illustrating light transmittance in the ultraviolet/visible/near-infrared regions of Formula 2.

FIG. 15 is a diagram illustrating light transmittance in the ultraviolet/visible/near-infrared regions of Formula 2. According to the diagram, a high transmittance of 80% or more is exhibited for all of the regions of about 350 nm or more. This compound also has a practical level of light transmittance.

The specimen used for measuring light transmittance was a thin film. The method for fabricating the TTP(COOH)$_2$ organic transparent thin film is as follows.

A solution prepared by dissolving TTP(COOH)$_2$ (0.47 mg, 1 mmol) in dimethyl sulfoxide (DMSO, 5 mL) was dropped in an amount of 0.1 µL to 1 µL onto a glass substrate to obtain a transparent thin-film electrode having a transmittance of more than 80% in a wavelength region of 300 to 2000 nm. The photograph in the drawing is of a thin-film electrode fabricated by dropping 2 µL.

[Quasi Closed-Shell Configuration]

A quasi closed-shell configuration is realized due to self-assembly of open-shell radicals in closed-shell molecules with a hydrogen bond network composed of an acid and a base, which are the key to carrier generation. The term quasi closed-shell configuration refers to an electron configuration that is seen, for example, in the transition metal d orbital and especially in the rare earth metal f orbital. In this configuration, spin is not involved in chemical bonding, has a low orbital energy, and is isolated and localized inside the atomic orbital due to being shielded by other electrons having a higher energy state. This induces a strong electron correlation effect in a solid state, which is a source of the exhibition of high physical properties peculiar to strongly-correlated system metals. This system is also called a "heavy electron system" because it increases the effective mass of electrons due to the strong electron correlation effect. A series of compounds that have been described above belong to the f electron system metal that has for the first time been realized in the state of organic solid.

The electron state according to an unlimited Hartree-Fock method (UHF)/6-31G* that uses a model in which one molecule of radical species TTP.$^+$COO.NH$_4$ is embedded in a tetramer of TTPCOO.NH$_4$ salt will now be described. It was learned that the singly occupied molecular orbital (SOMO) of the radical species was not present at the frontier orbital but localized at a more stabilized orbital. This quasi closed-shell configuration is exhibited for compounds having an arrangement in which a radical species is embedded in a supermolecular sequence that utilizes hydrogen bonds.

Examples of such substances that can be considered to exhibit an effect as a synthetic metal are listed below. In the following formulae, $R_1$, $R_2$, $R_3$, and $R_4$ may be the same or different. Based on the past knowledge about material science, the reasons why these compounds, like the above-described synthesized compounds, exhibit an effect as a synthetic metal is that it is thought that these substances are capable of self-assembly due to hydrogen bonds, and that there is a high likelihood that proton defects may be produced there, and this fact means that delocalized molecular spin is generated in a similarly-expanded π-conjugated site, whereby the substances act as a synthetic metal.

[Formula 4A]

Pattern 1
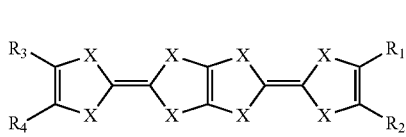

Pattern 2
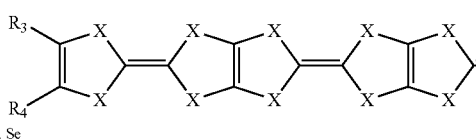

Pattern 3

X = S, Se
$R_1$ = COONH$_4$, SO$_3$NH$_4$, P(=O)ORONH$_4$, P(=S)ORONH$_4$, R = H, Me, Et, Pr, Bu
$R_2$ = COONH$_4$, SO$_3$NH$_4$, P(=O)ORONH$_4$, P(=S)ORONH$_4$, R = H, Me, Et, Pr, Bu
$R_3$ = COONH$_4$, SO$_3$NH$_4$, P(=O)ORONH$_4$, P(=S)ORONH$_4$, R = H, Me, Et, Pr, Bu
$R_4$ = COONH$_4$, SO$_3$NH$_4$, P(=O)ORONH$_4$, P(=S)ORONH$_4$, R = H, Me, Et, Pr, Bu

[Formula 5A]

Pattern 1
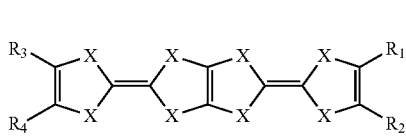

Pattern 2
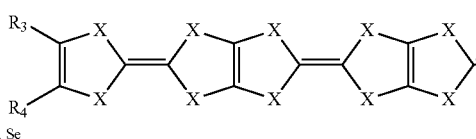

Pattern 3

X = S, Se
$R_1$ = COOH, SO$_3$H, P(=O)OROH, P(=S)OROH, R = H, Me, Et, Pr, Bu
$R_2$ = COOH, SO$_3$H, P(=O)OROH, P(=S)OROH, R = H, Me, Et, Pr, Bu
$R_3$ = COOH, SO$_3$H, P(=O)OROH, P(=S)OROH, R = H, Me, Et, Pr, Bu
$R_4$ = COOH, SO$_3$H, P(=O)OROH, P(=S)OROH, R = H, Me, Et, Pr, Bu

If the substance is a material that can act as a synthetic metal, then the substance can be used as an organic transparent electrode.

In addition, there are compounds that act as an organic transparent electrode even if they do not have the properties of a synthetic metal. The reason why such compounds can also be used as an organic transparent electrode is because they can maintain a conductivity of about 0.0001 S/cm or more, which allows a material to be widely applicable around room temperature.

Examples of such compounds that can be considered to exhibit an effect as an organic transparent electrode are listed below.

[Formula 4]

Pattern 1
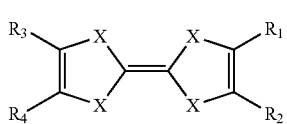

Pattern 2
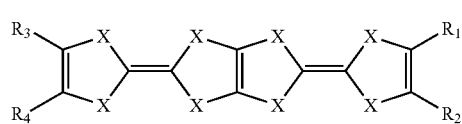

-continued

Pattern 3

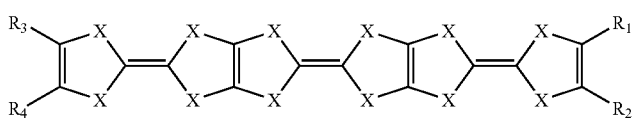

Pattern 4

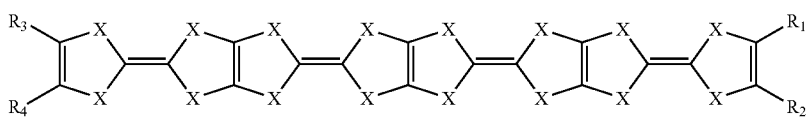

wherein

X is selected from the group consisting of S, O, and Se;

$R_1$ and $R_2$ are independently selected from the group consisting of H, COOH, $SO_3H$, $P(=O)OWOH$, in which W is selected from the group consisting of H, Me, Et, Pr, and Bu, CnHm, in which n is from 1 to 30, and m is from 3 to 61, QCnHm, in which Q is selected from the group consisting of O, S, and Se, n is from 1 to 30, and m is from 3 to 61,

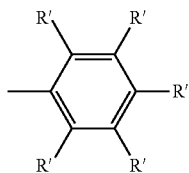

(R'=H, or QCnHm, in which Q is selected from the group consisting of O, S, and Se, n is from 1 to 30, and m is from 3 to 61),

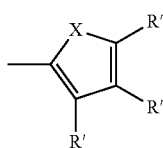

(R'=H, or QCnHm, in which Q is selected from the group consisting of O, S, and Se, n is from 1 to 30, and m is from 3 to 61), and

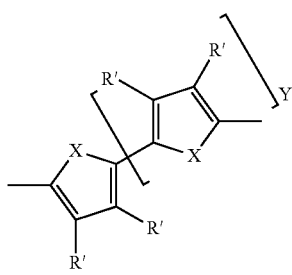

(R'=H, or QCnHm, in which Q is selected from the group consisting of O, S, and Se, n is from 1 to 30, m is from 3 to 61, and Y is from 1 to 50), or alternatively $R_1$ and $R_2$ are taken together to form —CnHm-, in which n is from 1 to 30, and m is from 3 to 61, -QCnHmQ-, -QCnHm-, in which Q is selected from the group consisting of O, S, and Se, n is from 1 to 30, and m is from 3 to 61, or -[Q(CnHm)i]j-, in which Q is selected from the group consisting of O, S, and Se, n is from 1 to 30, m is from 3 to 61, i is from 1 to 30, and j is from 1 to 30; and $R_3$ and $R_4$ are independently selected from the group consisting of H, COOH, $SO_3H$, $P(=O)OWOH$, in which W is selected from the group consisting of H, Me, Et, Pr, and Bu, CnHm, in which n is from 1 to 30, and m is from 3 to 61, QCnHm, in which Q is selected from the group consisting of O, S, and Se, n is from 1 to 30, and m is from 3 to 61,

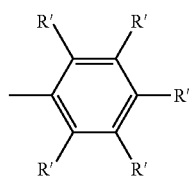

(R'=H, or QCnHm, in which Q is selected from the group consisting of O, S, and Se, n is from 1 to 30, and m is from 3 to 61),

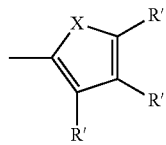

(R'=H, or QCnHm, in which Q is selected from the group consisting of O, S, and Se, n is from 1 to 30, and m is from 3 to 61), and

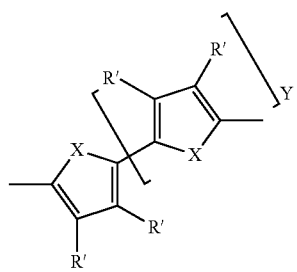

(R'=H, or QCnHm, in which Q is selected from the group consisting of O, S, and Se, n is from 1 to 30, m is from 3 to 61, and Y is from 1 to 50), or alternatively $R_3$ and $R_4$ are taken together to form —CnHm-, in which n is from 1 to 30, and m is from 3 to 61, -QCnHmQ-, -QCnHm-, in which Q is selected from the group consisting of O, S, and Se, n is from 1 to 30, and m is from 3 to 61, or -[Q(CnHm)i]j-, in which Q is selected from the group consisting of O, S, and Se, n is from 1 to 30, m is from 3 to 61, i is from 1 to 30, and j is from 1 to 30.

[Formula 8]

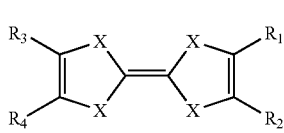
Pattern 1

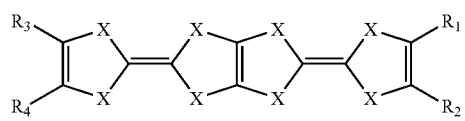
Pattern 2

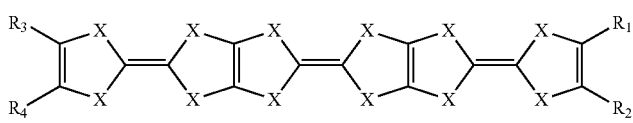
Pattern 3

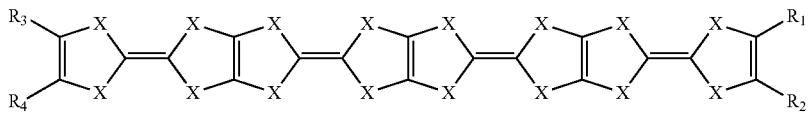
Pattern 4 wherein

X is selected from the group consisting of S, O, and Se;

$R_1$ and $R_2$ are independently selected from the group consisting of H, $COONH_4$, $COONH_3OH$, $COONH_3Z$, $SO_3NH_4$, $SO_3NH_3OH$, $SO_3NH_3Z$, $P(=O)OWONH_4$, in which W is selected from the group consisting of H, Me, Et, Pr, and Bu, $P(=O)OWONH_3OH$, in which W is selected from the group consisting of H, Me, Et, Pr, and Bu, $P(=O)OWONH_3Z$, in which W is selected from the group consisting of H, Me, Et, Pr, and Bu, and Z is Ph, or Ar, $NH_3A$, in which A is selected from the group consisting of F, Cl, Br, I, and $BF_4$, $CH(W)NH_3A$, in which W is selected from the group consisting of H, Me, Et, Pr, and Bu, and A is selected from the group consisting of F, Cl, Br, I, and $BF_4$, QCnHm, in which Q is selected from the group consisting of O, S, and Se, n is from 1 to 30, and m is from 3 to 61,

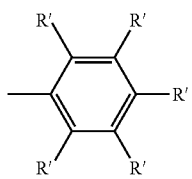

(R'=H, or QCnHm, in which Q is selected from the group consisting of O, S, and Se, n is from 1 to 30, and m is from 3 to 61),

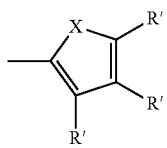

(R'=H, or QCnHm, in which Q is selected from the group consisting of O, S, and Se, n is from 1 to 30, and m is from 3 to 61), and

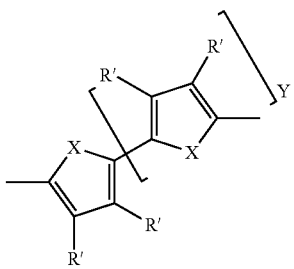

(R'=H, or QCnHm, in which Q is selected from the group consisting of O, S, and Se, n is from 1 to 30, m is from 3 to 61, and Y is from 1 to 50), or alternatively $R_1$ and $R_2$ are taken together to form —CnHm-, in which n is from 1 to 30, and m is from 3 to 61, -QCnHmQ-, -QCnHm-, in which Q is selected from the group consisting of O, S, and Se, n is from 1 to 30, and m is from 3 to 61, or -[Q(CnHm)i]j-, in which Q is selected from the group consisting of O, S, and Se, n is from 1 to 30, m is from 3 to 61, i is from 1 to 30, and j is from 1 to 30; and $R_3$ and $R_4$ are independently selected from the group consisting of H, $COONH_4$, $COONH_3OH$, $COONH_3Z$, $SO_3NH_4$, $SO_3NH_3OH$, $SO_3NH_3Z$, $P(=O)OWONH_4$, in which W is selected from the group consisting of H, Me, Et, Pr, and Bu, $P(=O)OWONH_3OH$, in which W is selected from the group consisting of H, Me, Et, Pr, and Bu, $P(=O)OWONH_3Z$, in which W is selected from the group consisting of H, Me, Et, Pr, and Bu, and Z is Ph, or Ar, $NH_3A$, in which A is selected from the group consisting of F, Cl, Br, I, and $BF_4$, $CH(W)NH_3A$, in which W is selected from the group consisting of H, Me, Et, Pr, and Bu, and A is selected from the group consisting of F, Cl, Br, I, and $BF_4$, QCnHm, in which Q is selected from the group consisting of O, S, and Se, n is from 1 to 30, and m is from 3 to 61,

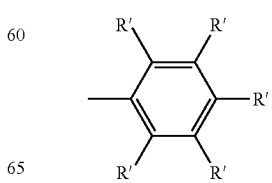

(R'=H, or QCnHm, in which Q is selected from the group consisting of O, S, and Se, n is from 1 to 30, and m is from 3 to 61),

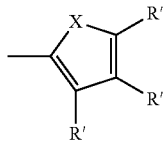

(R'=H, or QCnHm, in which Q is selected from the group consisting of O, S, and Se, n is from 1 to 30, and m is from 3 to 61), and

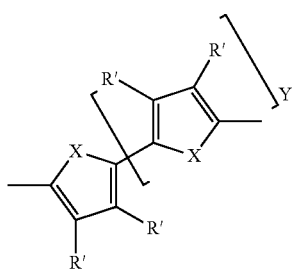

(R'=H, or QCnHm, in which Q is selected from the group consisting of O, S, and Se, n is from 1 to 30, m is from 3 to 61, and Y is from 1 to 50), or alternatively $R_3$ and $R_4$ are taken together to form —CnHm-, in which n is from 1 to 30, and m is from 3 to 61, -QCnHmQ-, -QCnHm-, in which Q is selected from the group consisting of O, S, and Se, n is from 1 to 30, and m is from 3 to 61, or -[Q(CnHm)i]j-, in which Q is selected from the group consisting of O, S, and Se, n is from 1 to 30, m is from 3 to 61, i is from 1 to 30, and j is from 1 to 30.

The substituent groups, such as $R_1$, $R_2$, $R_3$, $R_4$, and R', in the respective compounds may be the same or different.

[Synthesis Method]

Next, a specific synthesis method of the compounds will be described.

Figure 8:
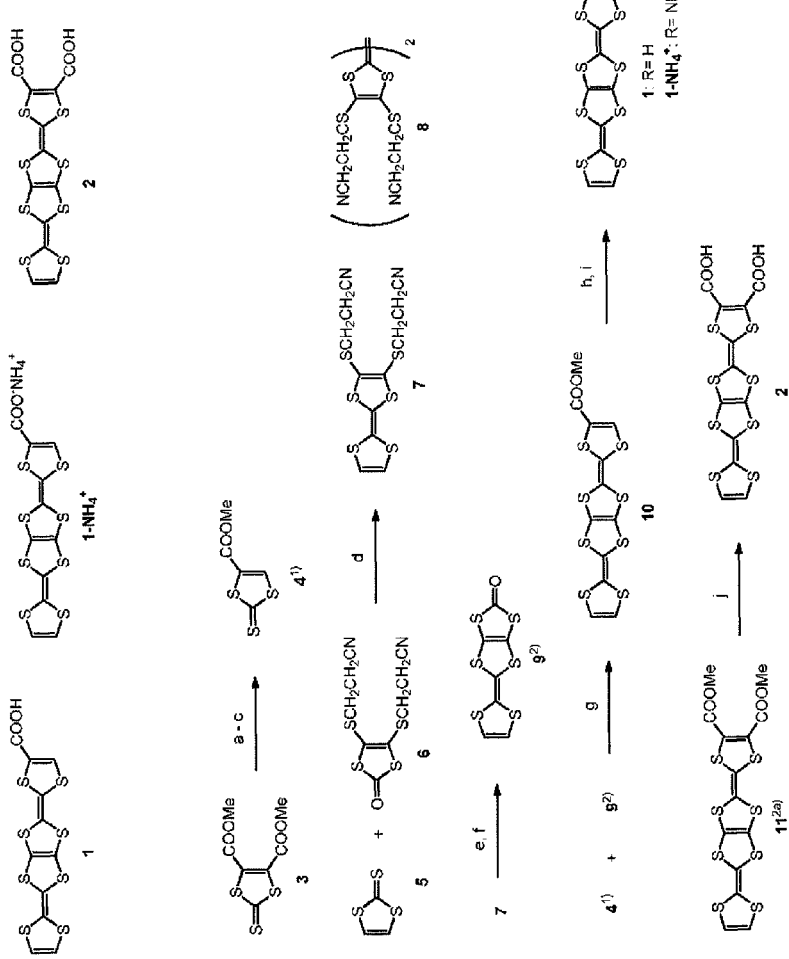
FIG. 8 is a diagram illustrating a synthesis scheme.
Figure 9:
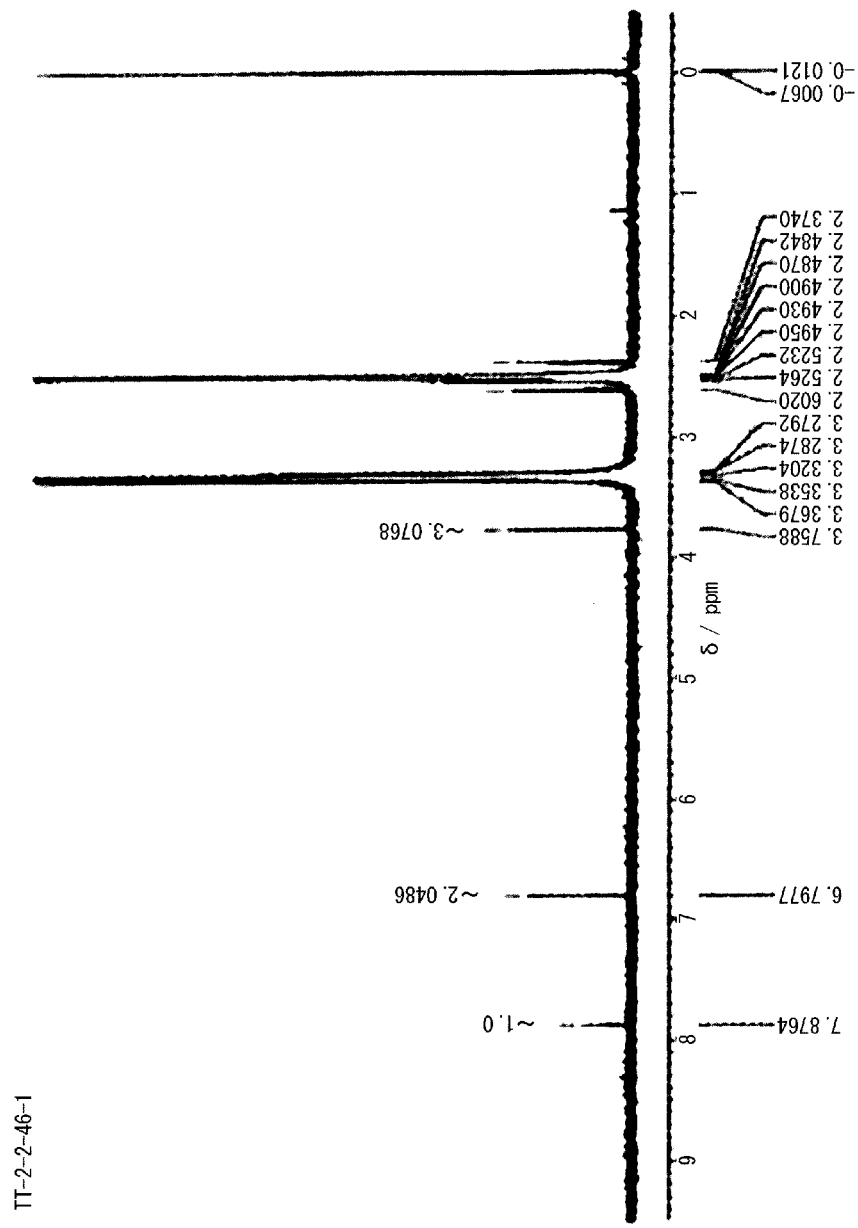
FIG. 9 is a diagram illustrating an NMR spectrum.
Figure 10:
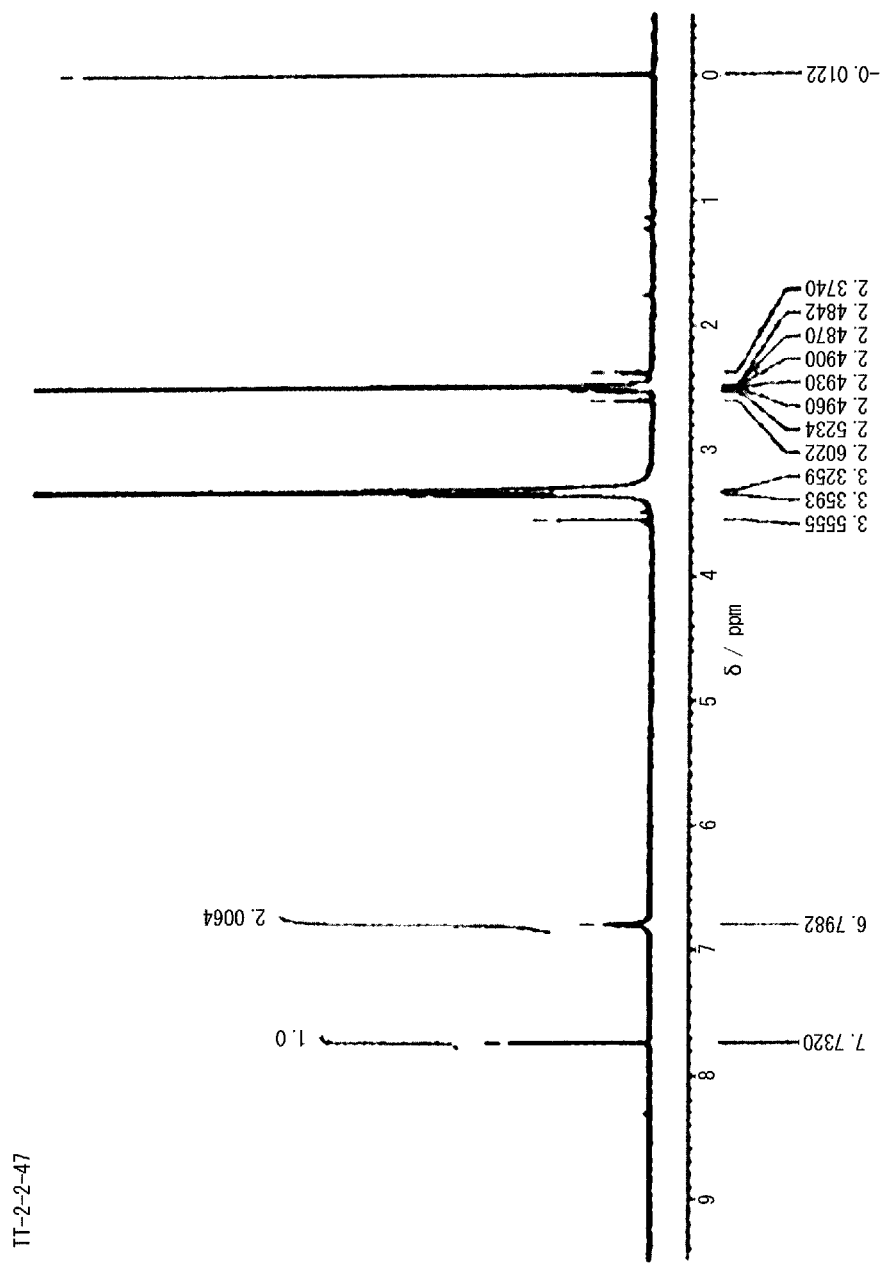
FIG. 10 is a diagram illustrating an NMR spectrum.
Figure 11:
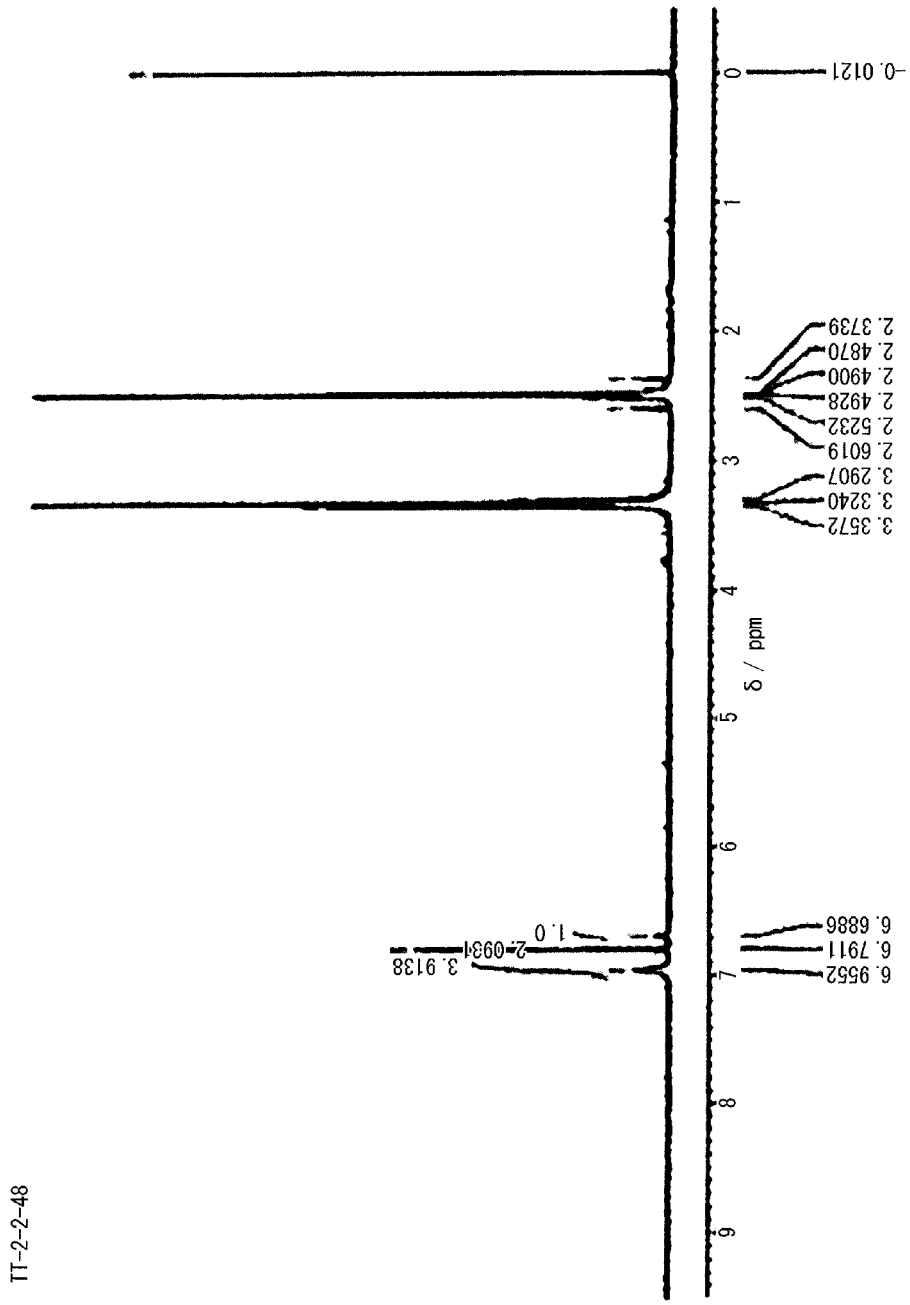
FIG. 11 is a diagram illustrating an NMR spectrum.
Figure 12:
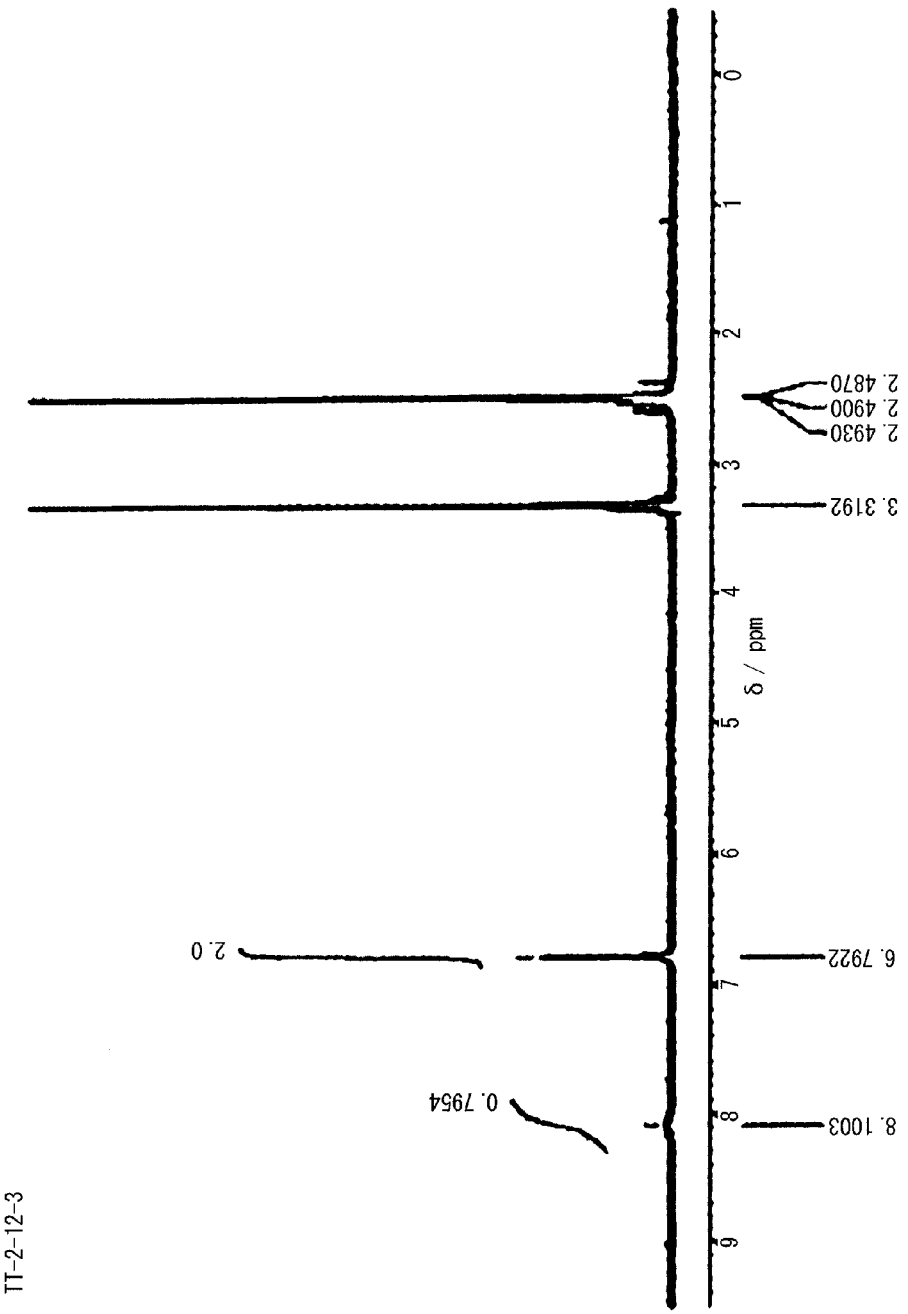
FIG. 12 is a diagram illustrating an NMR spectrum.

FIG. 8 is a diagram illustrating a synthesis scheme.

Methyl 2-{5-(1,3-dithiol-2-ylidene)-[1,3]dithiolo[4, 5-d][1,3]dithiol-2-ylidene}-1,3-dithiole-4-carboxylate (10)

$4^{1)}$ (45.8 mg, 0.238 mmol) and $9^{2)}$ (58.4 mg, 0.198 mmol) were suspended in a mixed solvent of trimethyl phosphite (3 ml) and toluene (3 ml). The resultant mixture was heated to reflux for 15 hours at 120° C., then left to cool to room temperature, and charged with n-hexane (6 ml). The mixture was left to stand for 2 hours at 5° C., and the deposit was filtered using a membrane filter (H010A047A, Advantec). The filtered product was successively washed with toluene, methanol, and chloroform. The filtered product was dried under reduced pressure to obtain a brown solid 10 (35.8 mg, yield based on 9 of 41%).

$^1$H NMR (600 MHz, DMSO-d6): δ 3.76 (s, 3H), 6.80 (s, 2H), 7.88 (s, 1H); Anal. calcd. for $C_{12}H_6O_2S_8$: C, 32.85; H, 1.38. Found: C, 32.47; H, 1.18.

2-{5-(1,3-Dithiol-2-ylidene)-[1,3]dithiolo[4,5-d][1, 3]dithiol-2-ylidene}-1,3-dithiole-4-carboxylic acid (1)

10 (125 mg, 0.285 mmol) was suspended in a mixed solvent of 1,4-dioxane (50 ml), THF (50 ml), and MeOH (50 ml). The resultant mixture was charged with 2 N LiOH (28.5 ml, 57.0 mmol). The mixture was vigorously stirred for 15 hours at room temperature, then 2 N HCl (28.5 ml) was gradually added dropwise, and the mixture was adjusted to a pH of 2 to 3 by further adding 2 N HCl (2.0 ml) while checking the pH. The mixture was stirred for 20 minutes at room temperature, and then filtered using a membrane filter (H010A047A, Advantec). The filtered product was successively washed with water, methanol, and then chloroform, and dried under reduced pressure to obtain the target product Compound 1 (110 mg, 91%) as a glossy silvery-red film-like solid.

$^1$H NMR (600 MHz, DMSO-d6): δ 6.80 (s, 2H), 7.73 (s, 1H); Anal. calcd. for $C_{11}H_4O_2S_8$: C, 31.11; H, 0.95. Found: C, 30.76; H, 0.82.

Ammonium 2-{5-(1,3-dithiol-2-ylidene)-[1,3]dithiolo[4,5-d][1,3]dithiol-2-ylidene}-1,3-dithiole-4-carboxylate (1-$NH_4^+$)

Finely crushed 1 (140 mg, 0.330 mmol) was suspended in a mixed solvent of 1,4-dioxane (31.5 ml), THF (31.5 ml), and $Et_2O$ (7.0 ml), and the resultant mixture was irradiated with ultrasonic waves for 15 seconds. The mixture was further charged with 28% aq. $NH_3$ (2.8 ml), and irradiated with ultrasonic waves for 15 seconds. The mixture was vigorously stirred for 14 hours at room temperature, and then left to stand for 1 hour at 5° C. The reaction mixture was then filtered using a membrane filter (H010A047A, Advantec). The filtered product was successively washed with water, THF, and $Et_2O$, and dried under reduced pressure to obtain the target product Compound 1-$NH_4^+$ (134 mg, 92%) as a dark red solid.

$^1$H NMR (600 MHz, DMSO-d6): δ 6.69 (brs, 1H), 6.79 (s, 2H), 6.96 (brs, 4H); Anal. calcd. for (TTFCOOH:NH3=2:1; $C_{22}H_{11}O_4NS_{16}$): C, 30.50; H, 1.28; N, 1.62. Found: C, 30.56; H, 1.03; N, 1.41.

2-{5-(1,3-Dithiol-2-ylidene)-[1,3]dithiolo[4,5-d][1, 3]dithiol-2-ylidene}-1,3-dithiole-4-carboxylic acid (2)

$11^{2a)}$ (20 mg, 0.0403 mmol) was suspended in a mixed solvent of 1,4-dioxane (4 ml), THF (2 ml), MeOH (2 ml), toluene (2 ml), and DMF (1 ml). The resultant mixture was charged with 2 N LiOH (800 μl, 1.60 mmol). The mixture was vigorously stirred for 3 days at room temperature, then 2 N HCl (800 μl) was gradually dropwise added thereto, and the mixture was adjusted to a pH of 4 by further adding thereto 2 N HCl (100 μl) while checking the pH. The mixture was stirred for 20 minutes at room temperature, and then filtered using a membrane filter (H010A047A, Advantec). The filtered product was successively washed with water, methanol, and chloroform, and dried under reduced pressure to obtain the target product Compound 2 (17.2 mg, 91%) as an umber brown solid.

$^1$H NMR (600 MHz, DMSO-d6): δ 6.79 (s, 2H); Anal. calcd. for $C_{12}H_4O_4S_8$: C, 30.75; H, 0.86. Found: C, 30.79; H, 1.19.

1) Pittman, Jr. C. U.; Narita, M.; Liang, Y. F. J. Org. Chem. 1976, 41, 2855-2860.
2) (a) Misaki Y.; Matsui, T.; Kawakami, K.; Nishikawa, H.; Yamabe, T.; Shiro, M. Chem. Lett. 1993, 1337-1340.
(b) Misaki Y.; Matsui, T.; Kawakami, K.; Fujiwara, H.; Yamabe, T.; Mori, T.; Mori, H.; Tanaka, S.; Shiro, M. Synth. Met. 1995, 70, 1149-1150.
(c) Aragaki, M.; Mori, T.; Misaki Y.; Tanaka, K.; Yamabe, T. Synth. Met. 1999, 102, 1601-1602.

(d) Bartlett, P. N.; Booth, S.; Caruana, D. J.; Kilburn, J. D.; Santamaria, C. Anal. Chem. 1997, 69, 734-742.

e) Olivier, J.; Golhen, S.; Swietlik, R.; Cador, O.; Pointillart, F.; Ouahab, L. Eur. J. Inorg. Chem. 2009, 3282-3290.

FIGS. 9, 10, 11, and 12 are diagrams illustrating NMR spectra, in which the structure of the compounds is also shown.

In the experiments, ESR measurement was performed under room temperature conditions on a small specimen obtained by pressure-forming and pelletizing a polycrystal of a spontaneously carrier doped salt, and the spin was quantified by comparing that ESR signal with the peak area of 2,2-diphenyl-1-picrylhydrazyl (commonly referred to as DPPH), which is a standard substance. The amounts of samples used are all normalized.

[Production Method of Substituted TTP Carboxylic Acid Derivative]

Next, the method for producing the substituted TTP carboxylic acid derivative according to the present invention will be described. The substituted TTP carboxylic acid according to the present invention can be produced, for example, by the following production method.

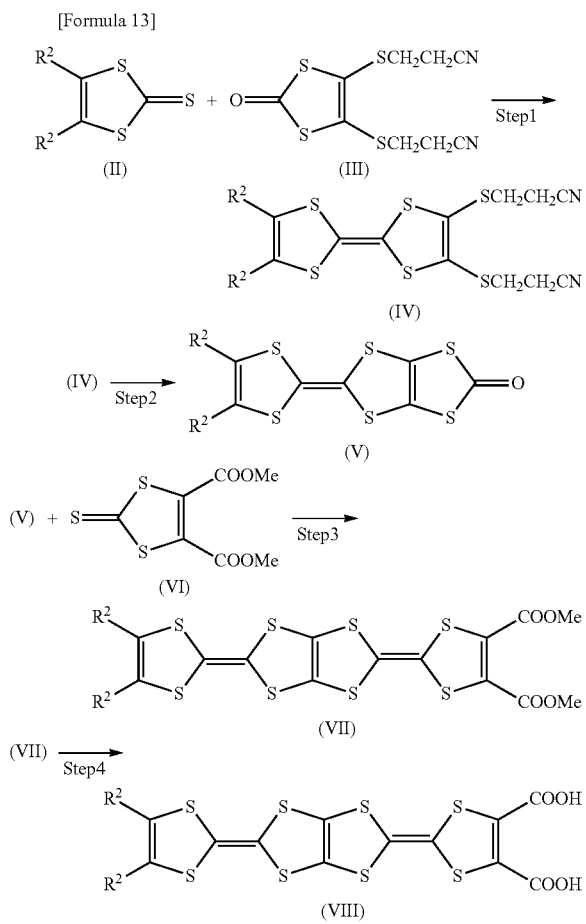

wherein $R^2$ represents a hydrogen atom, an alkyl group, an aryl group or the like.

(Step 1)

Compound (IV) can be produced by reacting Compound (II) and Compound (III) in the presence or absence of an inert solvent, in the presence of a reducing agent. Compound (II) may be commercially available or produced by the known method (e.g., P. Wu, G. Saito, K. Imaeda, Z. Shi, T. Mori, T. Enoki, H. Inokuchi, Chem. Lett., 15, 441-444 (1086), E. Gomar-Nadal, C. Rovira, D. B. Amabilino, Tetrahedron, 62, 3370-3379 (2006)), or a method described therein. Compound (III) may be commercially available or produced by the known method (e.g., H. Muller, C. Jouan, F. Salhi, Synth. Met., 85, 1457-1458 (1997)), or a method described therein.

Preferred examples of the inert solvent optionally used include a hydrocarbon such as benzene, toluene or xylene, an ether such as tetrahydrofuran, diethyl ether or dioxane, a polar organic solvent such as acetonitrile, N,N-dimethylformamide or hexamethylphosphoric triamide, or a mixed solvent of these organic solvents.

Preferred examples of the reducing agent include an organic reducing substance such as trimethyl phosphite, triethyl phosphite, triphenyl phosphine or trimethyl phosphine, a metal such as zinc, tin or aluminum, or an inorganic salt.

Although the reaction temperature mainly depends on the raw material compound or the type of the solvent used, usually, the reaction temperature is 0° C. to 200° C., preferably from room temperature to 120° C.

Although the reaction time mainly depends on the reaction temperature, the raw material compound, or the type of the solvent used, usually, the reaction time is 1 hour to 48 hours, preferably 2 hours to 12 hours.

(Step 2)

Compound (V) can be produced by reacting Compound (IV) obtained from Step 1 in an inert solvent in the presence of a base, and then reacting them in an inert solvent in the presence of a carbonylating agent.

Preferred examples of the inert solvent used herein include a hydrocarbon such as benzene, toluene or xylene, an ether such as tetrahydrofuran, diethyl ether or dioxane, a halogenated hydrocarbon such as chloroform or methylene chloride, a polar organic solvent such as acetonitrile, N,N-dimethylformamide or hexamethylphosphoric triamide, or a mixed solvent of these organic solvents.

Preferred examples of the base include an organic base such as triethylamine, diisopropylethylamine or pyridine, an inorganic base such as potassium carbonate, sodium hydrogen carbonate, cesium hydroxide, sodium hydroxide or tetrabutylammonium hydroxide, and a metal alkoxide such as sodium methoxide or potassium t-butoxide.

Preferred examples of the carbonylating agent include bis(trichloromethyl) carbonate, bis(4-nitrophenyl) carbonate, and N,N'-carbonyldiimidazole.

Although the reaction temperature mainly depends on the raw material compound or the type of the solvent used, usually, the reaction temperature is 0° C. to 200° C., preferably from room temperature to 60° C.

Although the reaction time mainly depends on the reaction temperature, the raw material compound, or the type of the solvent used, usually, the reaction time is 1 hour to 48 hours, preferably 2 hours to 24 hours.

(Step 3)

Compound (VII) can be produced by reacting Compound (V) obtained from Step 2 and Compound (VI) in the same manner as in Step 1, in the presence or absence of an inert solvent, in the presence of a reducing agent. Compound (VI) may be commercially available or produced by the known method (e.g., M. Ngounda, H. L. Bozec, P. Dixneuf, J. Org. Chem., 47, 4000-4002 (1982), F. M. Benitez, J. R. Grunwell, J. Org. Chem., 43, 2917-2918 (1978), L. R. Melby, H. D. Hartzler, W. A. Sheppard, J. Org. Chem., 39, 2456-2458 (1974)), or a method described therein.

(Step 4)

Compound (VIII) can be produced by reacting Compound (VII) obtained from Step 3 in an inert solvent in the presence of a base.

Preferred examples of the inert solvent include an alcohol such as methanol or ethanol, an ether such as tetrahydrofuran, diethyl ether or dioxane, a hydrocarbon such as benzene, toluene or xylene, a halogenated hydrocarbon such as chloroform or methylene chloride, a polar organic solvent such as N,N-dimethylformamide or hexamethylphosphoric triamide, or a mixed solvent of these organic solvents and water.

Preferred examples of the base include an organic base such as triethylamine, diisopropylethylamine or pyridine, an inorganic base such as potassium carbonate, sodium hydrogen carbonate, cesium hydroxide, sodium hydroxide or tetrabutylammonium hydroxide or a metal alkoxide such as sodium methoxide or potassium t-butoxide.

Although the reaction temperature mainly depends on the raw material compound or the type of the solvent used, usually, the reaction temperature is 0° C. to 200° C., preferably from room temperature to 60° C.

Although the reaction time mainly depends on the reaction temperature, the raw material compound, or the type of the solvent used, usually, the reaction time is 1 hour to 120 hours, preferably 12 hours to 72 hours.

EXAMPLES

The present invention will now be described in more detail with reference to the following working examples and test examples. However, the present invention should not be limited in any way to these working examples and test examples. Further, m.p. is an abbreviation for melting point.

Example 1

Preparation of dimethyl 2-[5-{4,5-bis(methylthio)-1, 3-dithiol-2-ylidene}-[1,3]dithiolo[4,5-d][1,3]dithiol-2-ylidene]-1,3-dithiole-4,5-dicarboxylate (Compound 2 of Compound No. 2 Indicated in the Table Shown Below (Hereinafter Indicated in the Same Manner))

(a) Preparation of 2,3-bis(2-cyanoethylthio)-6,7-bis (methylthio)-tetrathiafulvalene (Compound (a)) (Step 1)

Trimethyl phosphite (124 ml) was mixed with 4,5-bis(methylthio)-1,3-dithiol-2-thione (3.26 g, 14.4 mmol) (corresponding to Compound (II)) and 4,5-bis(2-cyanoethylthio)-1,3-dithiol-2-one (5.0 g, 17.3 mmol) (corresponding to Compound (III)) at room temperature. The resultant mixture was stirred for 3 hours at 120° C., and then insoluble matter was removed by filtration. The filtrate was dried under reduced pressure, and then purified by silica gel column chromatography (eluted with 100% toluene to toluene:ethyl acetate=10:1) to obtain the subject compound (a) (4.59 g, 68.3%) as a brown solid. Further, red-brown needle-like crystals of the subject compound (a) were obtained by recrystallizing from toluene/ethyl acetate.

m.p. 118-121° C.; $^1$H NMR (600 MHz, CDCl$_3$) δ 3.09 (t, J=7.1 Hz, 4H), 2.75 (t, J=7.1 Hz, 4H), 2.44 (s, 6H); $^{13}$C NMR (125 MHz, CDCl$_3$): δ=128.0, 127.6, 117.4, 114.6, 107.7, 31.3, 19.2, 18.9; IR (KBr) 2921, 2246, 1499, 1427, 1314, 1276, 1231, 975, 957, 896, 774 cm$^{-1}$; Anal. calcd. for C$_{14}$H$_{14}$N$_2$S$_8$: C, 36.02; H, 3.02; N, 6.00. Found: C, 36.09; H, 2.70; N, 5.86.

(b) Preparation of 5-(4,5-bis(methylthio)-1,3-dithiol-2-ylidene)-1,3,4,6-tetrathiapentalene (Compound (b)) (Step 2)

A mixed suspension of compound (a) (1.00 g, 2.14 mmol) (corresponding to Compound (IV)), acetone (10 ml), and methanol (10 ml) was mixed with a solution of 28% sodium methoxide in methanol (1.0 ml, 5.0 mmol). The resultant mixture was stirred for 30 minutes at room temperature, and then the obtained red solution was cooled to 0° C. To the solution, anhydrous zinc chloride (175 mg, 1.28 mmol) that had been previously dissolved in methanol (5 ml) and tetrabutylammonium bromide (830 mg, 2.57 mmol) that had been previously dissolved in methanol (5 ml) were added, and the mixture was then stirred for 20 minutes at room temperature. The solvent was removed by distillation under reduced pressure, then non-ionized water (30 ml) was added thereto to form a suspension. The suspension was filtered, then the solid matter obtained on the funnel was washed with non-ionized water and methanol, collected, and vacuum-dried. The dried solid mater was added to tetrahydrofuran (25 ml) to form a suspension, cooled to 0° C., and then mixed with bis(trichloromethyl) carbonate (520 mg, 1.75 mmol) that had been previously dissolved in tetrahydrofuran (5 ml). The mixture was stirred overnight at room temperature, then diluted by adding toluene (30 ml) and methanol (10 ml), and stirred for 10 minutes, after which the solvent was removed by distillation under reduced pressure. Then, the mixture was mixed with non-ionized water (20 ml) and methanol (20 ml), and stirred for 20 minutes at room temperature. The formed suspension was filtered, and the solid matter obtained on the funnel was washed with non-ionized water and methanol, then collected and vacuum-dried. The dried solid mater was added to diethyl ether (250 ml), irradiated with ultrasonic waves for 20 seconds, and stirred for 10 minutes at room temperature. The formed suspension was filtered, and the solid matter obtained on the funnel was washed with diethyl ether, then collected and vacuum-dried to obtain the subject compound (b) (388 mg, 46.9%) as a brown powder.

$^1$H NMR (600 MHz, CDCl$_3$) δ 2.44 (s, 6H); IR (KBr) 2918, 1667, 1618, 1428, 967, 893, 881, 764, 749 cm$^{-1}$; Anal. Calcd for C$_9$H$_6$OS$_8$: C, 27.96; H, 1.56. Found: C, 27.65; H, 1.21.

(c) Preparation of dimethyl 2-[5-{4,5-bis(methylthio)-1,3-dithiol-2-ylidene}-[1,3]dithiolo[4,5-d][1,3]dithiol-2-ylidene]-1,3-dithiole-4,5-dicarboxylate (Compound 2) (Step 3)

Trimethyl phosphite (50 ml) was mixed with compound (b) (1.00 g, 2.59 mmol) (corresponding to Compound (V)) and 1,3-dithiol-2-thione-4,5-dicarboxylate (1.00 g, 3.99 mmol) (corresponding to Compound (VI)) at room temperature. The resultant mixture was stirred for 14 hours at 120° C., then the temperature was returned to room temperature, and the solvent was removed by distillation under reduced pressure. The residue was suspended in diethyl ether (50 ml), and the resultant suspension was stirred for 30 minutes at room temperature. This suspension was filtered, and the solid matter obtained on the funnel was washed with diethyl ether. The washed solid mater was collected, dissolved in chloroform (350 ml), and purified by silica gel column chromatography (eluted with toluene) to obtain the subject Compound (1) (413 mg, 27.0%). Further, umber brown, plate-shaped crystals of Compound (2) were obtained by recrystallizing from chloroform.

m.p. 188° C. (dec.); $^1$H NMR (600 MHz, CDCl$_3$) δ 3.85 (s, 6H), 2.43 (s, 6H); $^{13}$C NMR (125 MHz, CDCl$_3$): δ=159.7, 131.9, 127.7, 116.3, 115.9, 115.3, 113.7, 113.0, 53.5, 19.3; IR (KBr) 2953, 1730, 1709, 1574, 1433, 1295, 1263, 1189, 1090, 1034, 764 cm$^{-1}$; Anal. Calcd for $C_{16}H_{12}O_4S_{10}$: C, 32.63; H, 2.05. Found: C, 32.60; H, 1.72; HRMS (ESI-TOF) m/z: [M+H]$^+$ Calcd for $C_{16}H_{13}O_4S_{10}$ 588.8015. Found 588.8024.

Example 2

Preparation of 2-[5-{4,5-bis(methylthio)-1,3-dithiol-2-ylidene}-[1,3]dithiolo[4,5-d][1,3]dithiol-2-ylidene]-1,3-dithiole-4,5-dicarboxylic acid (Compound 7) (Step 4)

Compound 1 (200 mg, 0.340 mmol) was suspended in a mixed solvent of tetrahydrofuran (40 ml) and methanol (4 ml), and the resultant suspension was mixed with an aqueous solution of 2 N sodium hydroxide (6.8 ml, 13.6 mmol). The mixture was stirred for 3 hours at 20° C., then 2 N aqueous hydrochloric acid (6.8 ml) was gradually added dropwise, and the mixture was adjusted to a pH of 2 to 3 by further adding 2 N aqueous hydrochloric acid (0.2 ml) while checking the pH. The mixture was stirred for 3 minutes at room temperature, and this suspension was filtered. The solid matter obtained on the funnel was successively washed with water, methanol, and then a small amount of toluene, collected and vacuum-dried to obtain the subject Compound 7 (159 mg, 83.2%) as a glossy silvery-red film-like solid.

$^1$H NMR (400 MHz, CDCl$_3$) δ 2.43 (s, 6H).

The structure of compounds obtained in the same manner as in the above-described Examples is shown in Table 1. In the table, Me is an abbreviation for a methyl group, and nBu is an abbreviation for a normal butyl group.

TABLE 1

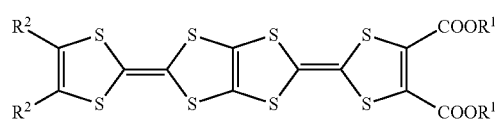

| Compound No. | R$^1$ | R$^2$ |
|---|---|---|
| 1 | Me | H |
| 2 | Me | S—Me |
| 3 | Me | S—CH$_2$—CH$_2$—S |
| 4 | Me | S—nBu |
| 5 | Me | S—nC$_{12}$H$_{25}$ |
| 6 | H | H |
| 7 | H | S—Me |
| 8 | H | S—CH$_2$—CH$_2$—S |
| 9 | H | S—nBu |
| 10 | H | S—nC$_{12}$H$_{25}$ |

The $^1$H-NMR spectra of the above compounds are shown in the following Table 2.

TABLE 2

| Compound No. | Measurement Solvent | $^1$H NMR [δ (ppm)] |
|---|---|---|
| 2 | CDCl$_3$ | 3.85 (s, 6H), 2.43 (s, 6H) |
| 3 | CDCl$_3$ | 3.85 (s, 6H), 3.30 (s, 4H) |
| 4 | CDCl$_3$ | 3.85 (s, 6H), 2.82 (t, J = 7.4 Hz, 4H), 1.61 (quin. J = 7.4 Hz, 4H), 1.44 (sext, J = 7.4 Hz, 4H), 0.93 (t, J = 7.4 Hz, 6H) |
| 5 | CDCl$_3$ | 3.85 (s, 6H) 2.81 (brt, J = 7.4 Hz, 4H), 1.65-1.58 (m, 4H), 1.42-1.36 (m, 4H), 1.32-1.22 (m, 32H), 0.88 (ddd, J = 7.1, 7.1, 1.6 Hz, 6H) |
| 7 | CDCl$_3$ | 2.43 (s, 6H) |
| 8 | DMSO-d$_6$ | 3.40 (s, 4H) |
| 9 | CDCl$_3$ | 2.82 (brt, J = 7.3 Hz, 4H), 1.70-1.52 (m, 4H), 1.52-1.38 (m, 4H), 0.93 (brt, J = 7.3 Hz, 6H) |
| 10 | CDCl$_3$ | 2.81 (br, 4H), 1.68-1.57 (m, 4H), 1.44-1.34 (m, 4H), 1.33-1.21 (m, 32H), 0.88 (brt, 6H) |

Test Example 1

Room Temperature Electrical Conductivity Measurement Test

Test Method

For Compounds 1, 7, 8, 9 and 10, a pellet sample (A) was prepared by crushing powder crystals with a pestle in a mortar and pressure-forming using a hydraulic pump. For Compounds 2 and 3, a single crystal sample (B) was obtained by gently evaporating the organic solvent. A gold wire having a diameter of 0.01 mm and a purity of 99% or more was arranged in a line at four locations on each test sample using a gold paste to provide terminals. Then, evaluation was carried out by measuring under room temperature conditions the voltage across the two middle points when a current of about 0.1 μA was applied. The value standardized based on sample size was taken as the test value.

Test Example 2

Room Temperature Mobility Measurement Test

Test Method

Terminals were provided by arranging two gold wires each having a diameter of 0.01 mm and a purity of 99% or more with gold paste on either end of sample A or B, and in an orthogonal direction to the line linking those two points, arranging two further gold wires with gold paste. Then, evaluation was carried out by measuring under room temperature conditions the voltage across the two middle points when a current of about 0.1 μA was applied across the terminals at either end. Hole mobility ($\mu_h$) is related to conductivity (σ), electric charge (e), and carrier density (n) based on the following formula. The value calculated using these was taken as the test value.

$$\sigma = e \ast n \ast \mu_h$$

The results from the above tests are shown in Table 3 shown below. In the table, regarding the sample shape symbols, A represents a pellet formed by pressure-forming of a powder crystal, and B represents a single crystal.

TABLE 3

| Compound No. | Sample Shape | Room Temperature Electrical Conductivity $\sigma_{RT}$(S/cm) | Room Temperature Mobility $\mu_{RT}$ (cm$^2$/V · s) |
|---|---|---|---|
| 1 | A | $2.0 \times 10^{-3}$ | 0.0866 |
| 2 | B | $5.0 \times 10^{-5}$ | 0.786 |
| 3 | B | $2.0 \times 10^{-4}$ | |
| 7 | A | $8.6 \times 10^{-2}$ | |
| 8 | A | 4.0 | |
| 9 | A | $1.5 \times 10^{-2}$ | |
| 10 | A | $1.5 \times 10^{-3}$ | |

Compounds 1 to 10 all exhibit excellent charge transport properties and solubility in an organic solvent, and can be formed as a thin film, while each is still a single molecule and a simple substance. Therefore, Compounds 1 to 10 hold promise for industrial applications in touch panels, transparent electrodes, and organic field-effect transistors.

[Applications]

The compounds according to the present embodiment can be used in various applications. Examples include in wiring, an information transmission medium, an electronic device, an electrode utilized in an electronic device, a spintronics device, an information communication device, a memory device, a magnetic shield, a medical magnetic shield, a magnet, a magnetic semiconductor, a field-effect transistor (FET), a sticking plaster that includes a magnet, a hard disk drive head, a high sensitivity playback GMR head, a solid-state magnetic memory, a magnetoresistive memory (MRAM), a fiber communication optical isolator, a material that changes color in a magnetic field, and a material that utilizes the interaction between conduction electron spin and atomic magnetic moment. Further examples include a touch panel, a display, an electronic device, a liquid crystal display, a flat-screen TV, a plasma display, electronic ink, an anode in an organic EL (hole injection layer), a solar cell, an antistatic agent, an electromagnetic shielding material, an optical coating, an infrared reflective material, a gas sensor, an antireflection film, a surface processing agent, a semiconductor laser, an optical device, an optical element, a device that utilizes bending resistance, an electrolytic capacitor, an electronic component, a lithium ion battery electrode, a light-emitting device, an organic transistor, and a printable circuit for directly forming a pattern on a substrate by utilizing ink jet technology or the like using a conductive polymer for ink.

Further, even if the compounds according to the present embodiment are not a single crystal, since they still exhibit high physical property values in a microcrystal pressure-formed state, it is suggested that the compounds according to the present embodiment can be converted into polymers and liquid crystals, and be formed into thin films. Thin-film forming carried out by coating opens up possibilities to many applications.

[Interpretation of Rights and the Like]

The present invention are described above with reference to specific embodiments. However, it is obvious that a person skilled in the art could make modifications and replacements to the embodiments within the scope of the present invention. Namely, the present invention is disclosed above in the form of examples, which should not be construed as limiting the subject matter of the specification. To determine the scope of the present invention, due consideration should be given to the claims described at the top.

Further, although it is clear that the embodiments for describing the invention achieve the above-described objectives, it should be understood that a person skilled in the art could implement many changes and other working examples. The elements and components in the claims, the specification, and the drawings, and each of the embodiments for description may be used with another one or a combination of other ones. The claims are intended to include such changes and other embodiments, which are included in the technical concept and the technical scope of this invention.

The invention claimed is:

1. A synthetic metal comprising
   an organic molecule having an electron-donating ability, and a π-conjugated plane, and being self-assembling, wherein the organic molecule is selected from the group consisting of:
   (i) compounds represented by Formula 4A, wherein $R_1$, $R_2$, $R_3$, and $R_4$ may be the same or different:

Formula 4A

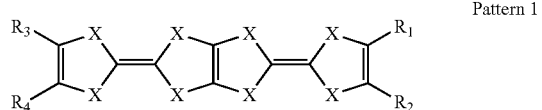

Pattern 1

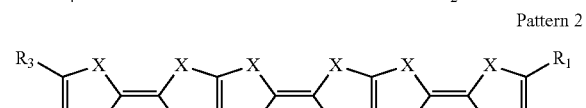

Pattern 2

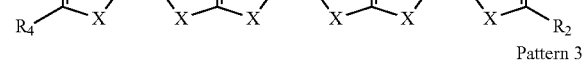

Pattern 3

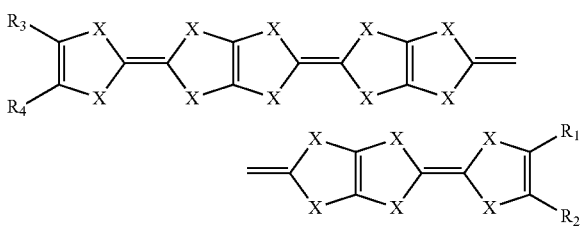

wherein
   X is S or Se; and
   $R_1$, $R_2$, $R_3$ and $R_4$ are Brønsted acid functional groups independently selected from the group consisting of COONH$_4$, SO$_3$NH$_4$, P(═O)ORONH$_4$, in which R is selected from the group consisting of H, Me, Et, Pr, and Bu, and P(═S)ORONH$_4$, in which R is selected from the group consisting of H, Me, Et, Pr, and Bu;
   (ii) compounds represented by Formula 5A, wherein $R_1$, $R_2$, $R_3$, and $R_4$ may be the same or different, or a salt thereof:

Formula 5A

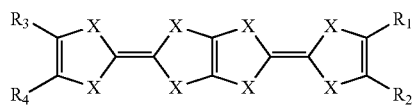

Formula 4

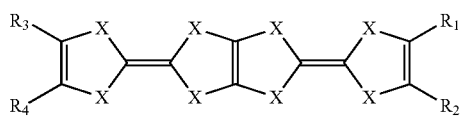

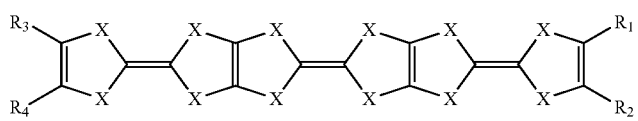

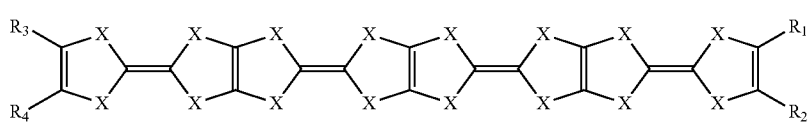

-continued

Pattern 2

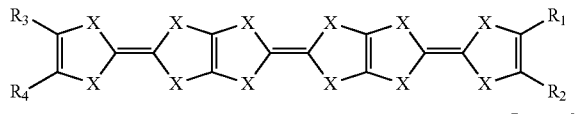

Pattern 3

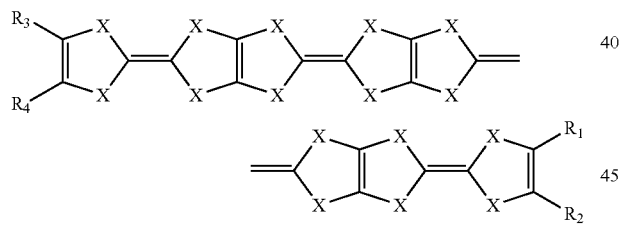

wherein
X is S or Se; and
$R_1$, $R_2$, $R_3$ and $R_4$ are Brønsted acid functional groups independently selected from the group consisting of COOH, $SO_3H$, $P(=O)OROH$, in which R is selected from the group consisting of H, Me, Et, Pr, and Bu, and $P(=S)OROH$, in which R is selected from the group consisting of H, Me, Et, Pr, and Bu; and
(iii) a compound represented by Formula 3A:

Formula 3A

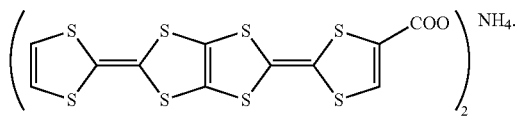

2. An organic transparent electrode comprising
an organic molecule having an electron-donating ability, and a π-conjugated plane, and being self-assembling, wherein the organic molecule is selected from the group consisting of:

(i) compounds represented by Formula 4, wherein $R_1$, $R_2$, $R_3$, $R_4$, and R' may be the same or different, or a salt thereof:

Pattern 1

Pattern 2

Pattern 3

Pattern 4 wherein
X is selected from the group consisting of S, O, and Se;
$R_1$ and $R_2$ are independently selected from the group consisting of H, COOH, $SO_3H$, $P(=O)OWOH$, in which W is selected from the group consisting of H, Me, Et, Pr, and Bu, CnHm, in which n is from 1 to 30, and m is from 3 to 61, QCnHm, in which Q is selected from the group consisting of O, S, and Se, n is from 1 to 30, and m is from 3 to 61,

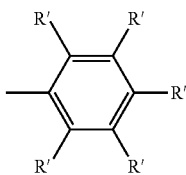

(R'=H, or QCnHm, in which Q is selected from the group consisting of O, S, and Se, n is from 1 to 30, and m is from 3 to 61),

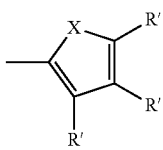

(R'=H, or QCnHm, in which Q is selected from the group consisting of O, S, and Se, n is from 1 to 30, and m is from 3 to 61), and

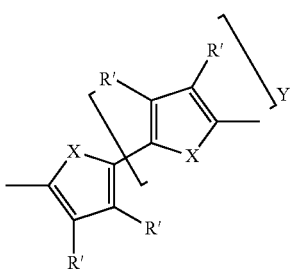

(R'=H, or QCnHm, in which Q is selected from the group consisting of O, S, and Se, n is from 1 to 30, m is from 3 to 61, and Y is from 1 to 50), or alternatively $R_1$ and $R_2$ are taken together to form —CnHm-, in which n is from 1 to 30, and m is from 3 to 61, or -QCnHm-, in which Q is selected from the group consisting of O, S, and Se, n is from 1 to 30, and m is from 3 to 61; and $R_3$ and $R_4$ are independently selected from the group consisting of H, COOH, $SO_3H$, $P(=O)OWOH$, in which W is selected from the group consisting of H, Me, Et, Pr, and Bu, CnHm, in which n is from 1 to 30, and m is from 3 to 61, QCnHm, in which Q is selected from the group consisting of O, S, and Se, n is from 1 to 30, and m is from 3 to 61,

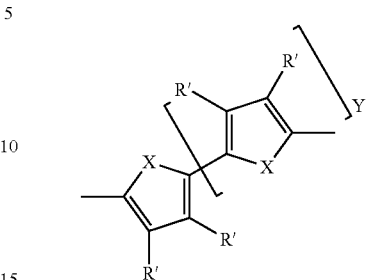

(R'=H, or QCnHm, in which Q is selected from the group consisting of O, S, and Se, n is from 1 to 30, m is from 3 to 61, and Y is from 1 to 50), wherein at least one of $R_1$, $R_2$, $R_3$ and $R_4$ is a Brønsted acid functional group selected from the group consisting of COOH, $SO_3H$, and $P(=O)OWOH$;

(ii) compounds represented by Formula 8, wherein $R_1$, $R_2$, $R_3$, $R_4$, and R' may be the same or different:

Formula 8

Pattern 2
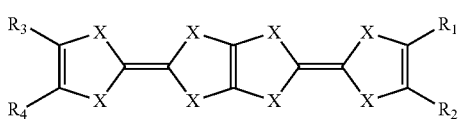

Pattern 3
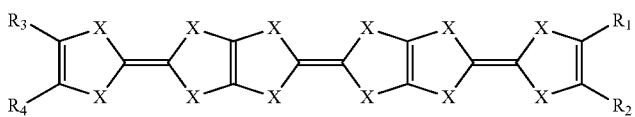

Pattern 4
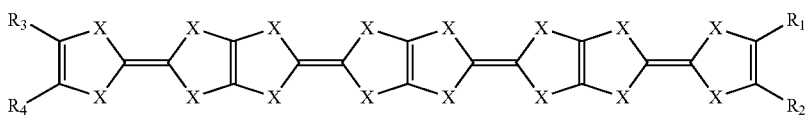

wherein

X is selected from the group consisting of S, O, and Se;

$R_1$ and $R_2$ are independently selected from the group consisting of H, $COONH_4$, $COONH_3OH$, $COONH_3Z$, $SO_3NH_4$, $SO_3NH_3OH$, $SO_3NH_3Z$, $P(=O)OWONH_4$, in which W is selected from the group consisting of H, Me, Et, Pr, and Bu, $P(=O)OWONH_3OH$, in which W is selected from the group consisting of H, Me, Et, Pr, and Bu, $P(=O)OWONH_3Z$, in which W is selected from the group consisting of H, Me, Et, Pr, and Bu, and Z is Ph, or Ar, $NH_3A$, in which A is selected from the group consisting of F, Cl, Br, I, and $BF_4$, $CH(W)NH_3A$, in which W is selected from the group consisting of H, Me, Et, Pr, and Bu, and A is selected from the group consisting of F, Cl, Br, I, and $BF_4$, QCnHm, in which Q is selected from the group consisting of O, S, and Se, n is from 1 to 30, and m is from 3 to 61,

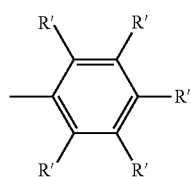

(R'=H, or QCnHm, in which Q is selected from the group consisting of O, S, and Se, n is from 1 to 30, and m is from 3 to 61),

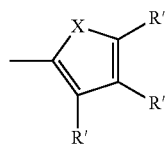

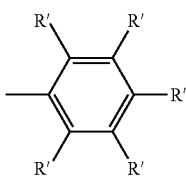

(R'=H, or QCnHm, in which Q is selected from the group consisting of O, S, and Se, n is from 1 to 30, and m is from 3 to 61),

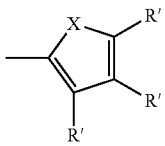

(R'=H, or QCnHm, in which Q is selected from the group consisting of O, S, and Se, n is from 1 to 30, and m is from 3 to 61), and

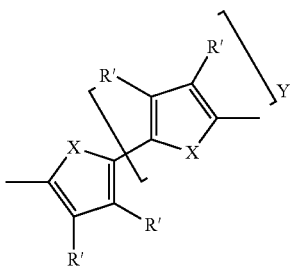

(R'=H, or QCnHm, in which Q is selected from the group consisting of O, S, and Se, n is from 1 to 30, m is from 3 to 61, and Y is from 1 to 50), or alternatively $R_1$ and $R_2$ are taken together to form —CnHm-, in which n is from 1 to 30, and m is from 3 to 61, or -QCnHm-, in which Q is selected from the group consisting of O, S, and Se, n is from 1 to 30, and m is from 3 to 61; and $R_3$ and $R_4$ are independently selected from the group consisting of H, $COONH_4$, $COONH_3OH$, $COONH_3Z$, $SO_3NH_4$, $SO_3NH_3OH$, $SO_3NH_3Z$, $P(=O)OWONH_4$, in which W is selected from the group consisting of H, Me, Et, Pr, and Bu, $P(=O)OWONH_3OH$, in which W is selected from the group consisting of H, Me, Et, Pr, and Bu, $P(=O)OWONH_3Z$, in which W is selected from the group consisting of H, Me, Et, Pr, and Bu, and Z is Ph, or Ar, $NH_3A$, in which A is selected from the group consisting of F, Cl, Br, I, and $BF_4$, $CH(W)NH_3A$, in which W is selected from the group consisting of H, Me, Et, Pr, and Bu, and A is selected from the group consisting of F, Cl, Br, I, and $BF_4$, QCnHm, in which Q is selected from the group consisting of O, S, and Se, n is from 1 to 30, and m is from 3 to 61,

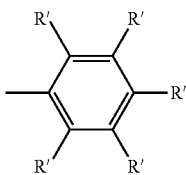

(R'=H, or QCnHm, in which Q is selected from the group consisting of O, S, and Se, n is from 1 to 30, and m is from 3 to 61),

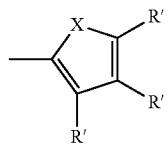

(R'=H, or QCnHm, in which Q is selected from the group consisting of O, S, and Se, n is from 1 to 30, and m is from 3 to 61), and

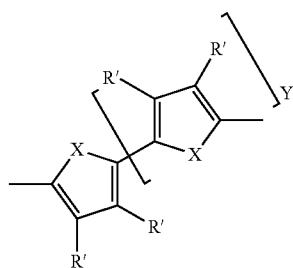

(R'=H, or QCnHm, in which Q is selected from the group consisting of O, S, and Se, n is from 1 to 30, m is from 3 to 61, and Y is from 1 to 50), wherein at least one of $R_1$, $R_2$, $R_3$ and $R_4$ is a Brønsted acid functional group selected from the group consisting of $COONH_4$, $COONH_3OH$, $COONH_3Z$, $SO_3NH_4$, $SO_3NH_3OH$, $SO_3NH_3Z$, $P(=O)OWONH_4$, $P(=O)OWONH_3OH$, and $P(=O)OWONH_3Z$; and (iii) a compound represented by Formula 3:

Formula 3

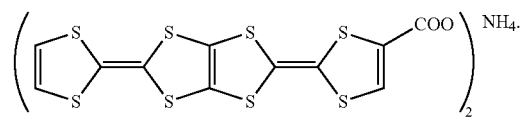

3. The organic transparent electrode according to claim 2, wherein said organic molecule is a compound represented by Formula 2 or a salt thereof:

Formula 2

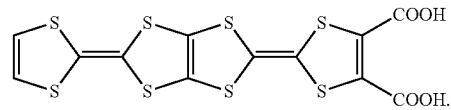

4. The synthetic metal according to claim 1, wherein said organic molecule is a compound represented by Formula 2A or a salt thereof Formula 2A
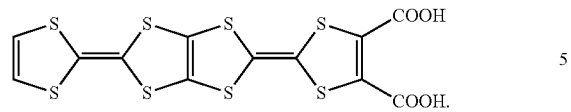
5. A wire comprising the synthetic metal according to claim 4.
6. An electronic device comprising the synthetic metal according to claim 4.
* * * * *